(12) United States Patent
Johnson

(10) Patent No.: US 6,938,461 B1
(45) Date of Patent: Sep. 6, 2005

(54) CONSTANT-HEAD SOIL PERMEAMETER FOR DETERMINING THE HYDRAULIC CONDUCTIVITY OF EARTHEN MATERIALS AT A WIDE RANGE OF DEPTHS

(76) Inventor: Larry K. Johnson, 4424 Middle Ridge Dr., Fairfax, VA (US) 22033

( * ) Notice: Subject to any disclaimer, the term of this patent is extended or adjusted under 35 U.S.C. 154(b) by 0 days.

(21) Appl. No.: 10/449,412

(22) Filed: Jun. 2, 2003

Related U.S. Application Data

(63) Continuation-in-part of application No. 09/764,375, filed on Jan. 19, 2001, now Pat. No. 6,571,605.

(51) Int. Cl.$^7$ .............................................. G01N 15/08
(52) U.S. Cl. ........................ 73/38; 73/37; 73/73; 73/74
(58) Field of Search ................................ 73/37, 38, 73, 73/74

(56) References Cited

U.S. PATENT DOCUMENTS

| | | |
|---|---|---|
| 2,949,766 A | 8/1960 | Kirkham et al. |
| 3,241,357 A * | 3/1966 | Kellner et al. .................. 73/38 |
| 3,892,126 A | 7/1975 | Curtain |
| 3,898,872 A * | 8/1975 | Skaling et al. .................. 73/73 |
| 3,926,143 A | 12/1975 | Hothan |
| 3,954,612 A | 5/1976 | Wilkerson |
| 4,182,157 A | 1/1980 | Fink |
| 4,341,110 A | 7/1982 | Block |
| 4,520,657 A | 6/1985 | Marthaler |
| 4,561,290 A | 12/1985 | Jewell |
| 4,829,817 A | 5/1989 | Kozlowski |
| 4,884,436 A | 12/1989 | Ankeny et al. |

(Continued)

FOREIGN PATENT DOCUMENTS

| | | | |
|---|---|---|---|
| DE | 4435019 A1 * | 3/1995 | .......... G01N 33/24 |

(Continued)

OTHER PUBLICATIONS

A. Amoozegar, "A Compact Constant-Head Permeameter for Mesuring Saturated Hydraulic Conductivty of the Vadoso Zone", *Soil Science Society of America Journal*, vol. 53, No. 5, Sep.-Oct. 1989, pp. 1356-1361.

(Continued)

*Primary Examiner*—Hezron Williams
*Assistant Examiner*—David Rogers
(74) *Attorney, Agent, or Firm*—Marion P. Lelong

(57) ABSTRACT

A constant-head soil permeameter for determining hydraulic conductivity of earthen materials is inserted into a borehole at the desired test depth. A calibrated reservoir, disposed on the ground surface, is attached thereto with a suitable length of hose. Water is added to the calibrated reservoir and allowed to flow freely into the borehole until an equilibrium level is reached in the borehole and inside the soil permeameter. The water flowing to the permeameter is throttled by buoyant float pressure that is greatly increased by a single lever, lever-lever, or lever-link-lever valve control assembly which provides considerable versatility and mechanical advantage, thereby allowing more constant head control and much greater depths of testing than previously attained by known permeameters. A filtered vent system, backflow check valve, and seals restrict entry of soil particles and debris, thereby minimizing cleaning and maintenance of the invention. The soil permeability is determined by solving appropriate mathematical equations which utilize the equilibrium height of water, rate of water flow, and dimensions of the borehole as input parameters.

28 Claims, 21 Drawing Sheets

U.S. PATENT DOCUMENTS

| | | | |
|---|---|---|---|
| 4,956,993 A * | 9/1990 | Mehler | 73/38 |
| 4,984,447 A | 1/1991 | Phillips | |
| 5,161,407 A | 11/1992 | Ankeny et al. | |
| 5,520,248 A | 5/1996 | Sissoin et al. | |
| 5,758,538 A * | 6/1998 | Hubbell et al. | 73/73 |
| 5,780,720 A * | 7/1998 | Swain | 73/38 |
| 5,915,476 A * | 6/1999 | Hubbell et al. | 166/113 |
| 5,941,121 A * | 8/1999 | Faybishenko | 73/73 |
| 6,055,850 A | 5/2000 | Turner et al. | |
| 6,098,448 A | 8/2000 | Lowry et al. | |
| 6,105,418 A | 8/2000 | Kring | |
| 6,178,808 B1 | 1/2001 | Wang et al. | |
| 6,212,941 B1 | 4/2001 | Cholet | |
| 6,393,908 B1 * | 5/2002 | Swain et al. | 73/216 |
| 6,405,588 B1 * | 6/2002 | Hubbell et al. | 73/152.46 |
| 2002/0007951 A1 * | 1/2002 | Learned | 166/332.8 |

FOREIGN PATENT DOCUMENTS

| | | | | |
|---|---|---|---|---|
| JP | 63175742 A | * | 7/1988 | G01N 15/08 |
| JP | 2002021059 A | * | 1/2002 | E02D 1/08 |

OTHER PUBLICATIONS

A. Amoozegar, "Comparison of the Glover Solution with the Simultaneous-Equations Approach for Measuring Hydraulic Conductivity," *Soil Science Society of America Journal*, vol. 53, No. 5, pp. 1362-1367, Sep.-Oct. 1989.

* cited by examiner

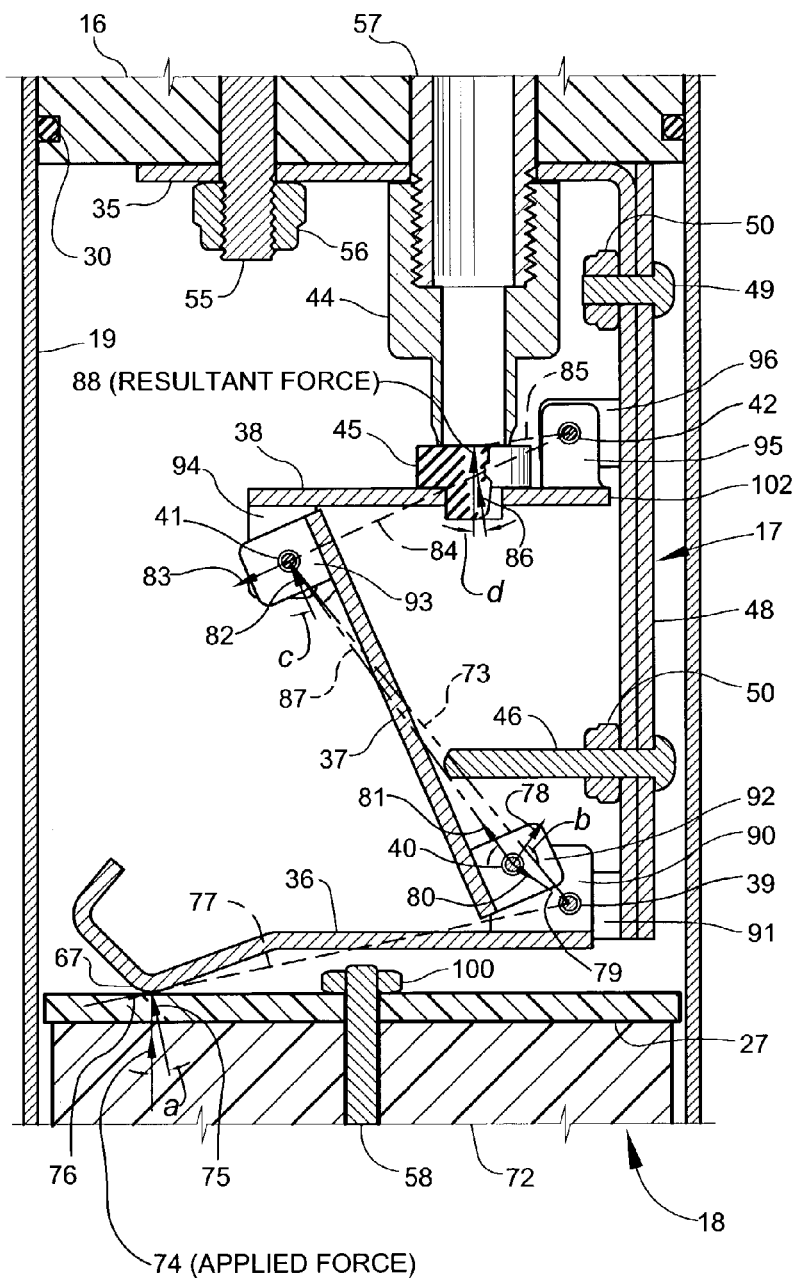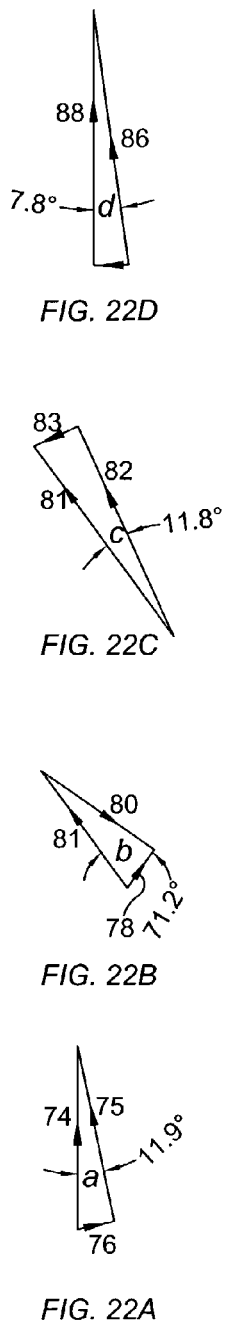
FIG. 22

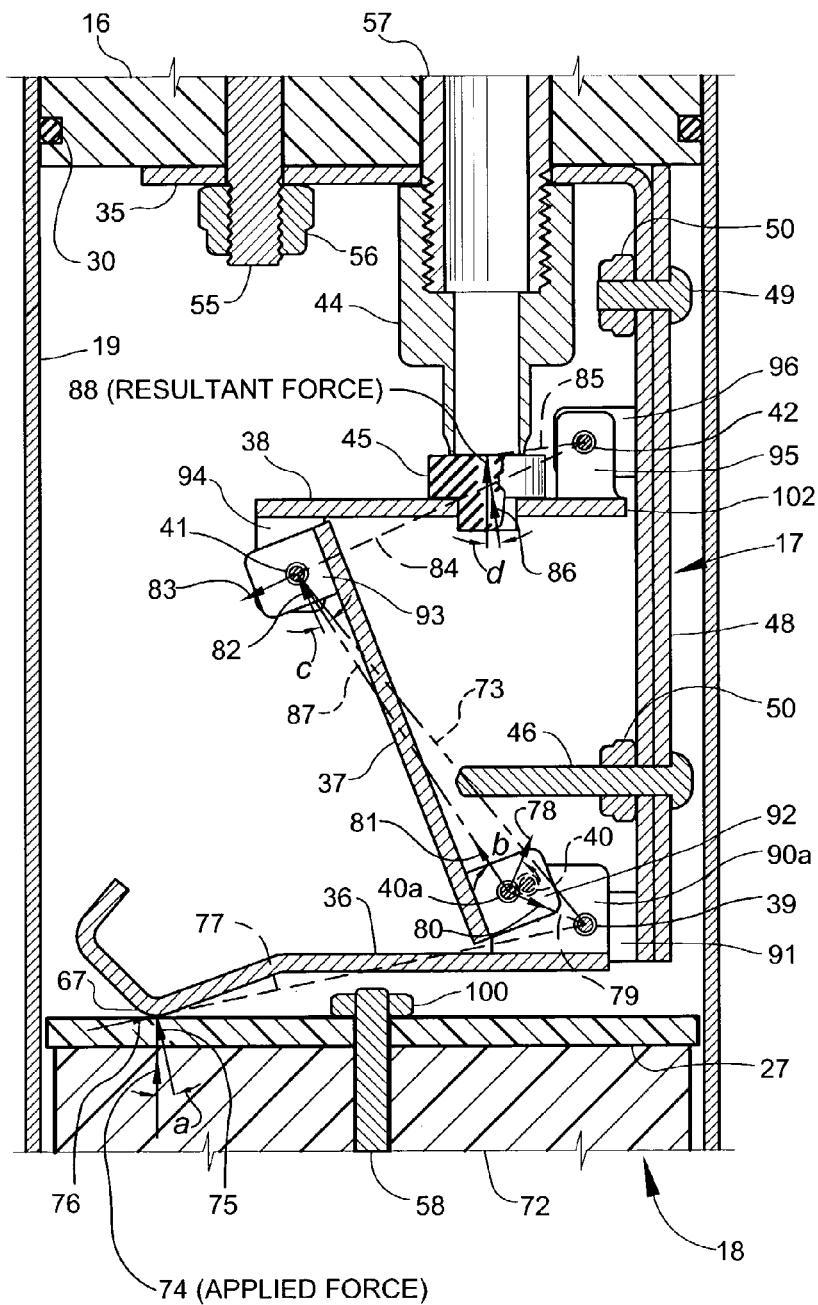
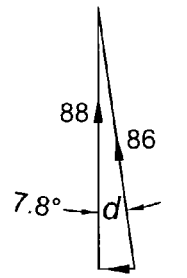
FIG. 23D
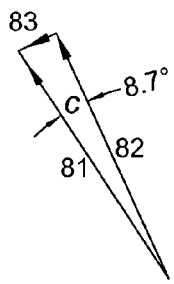
FIG. 23C
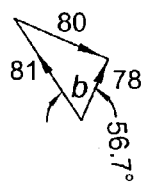
FIG. 23B
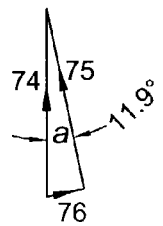
FIG. 23A
FIG. 23

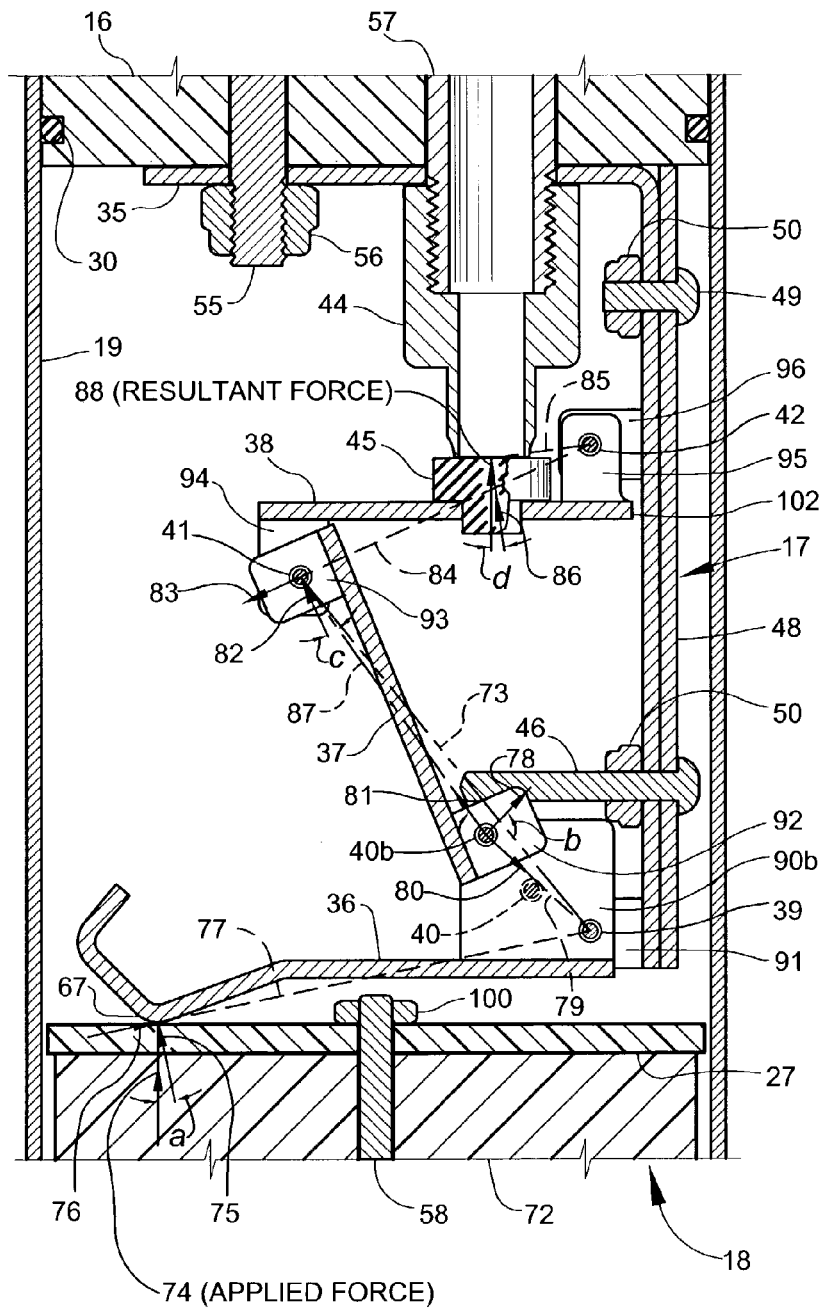
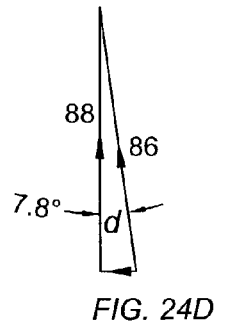
FIG. 24D
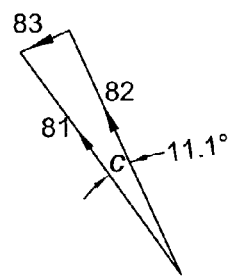
FIG. 24C
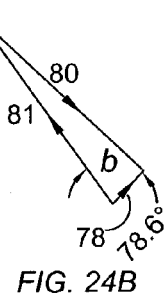
FIG. 24B
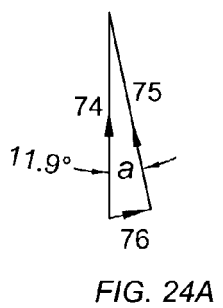
FIG. 24A
FIG. 24

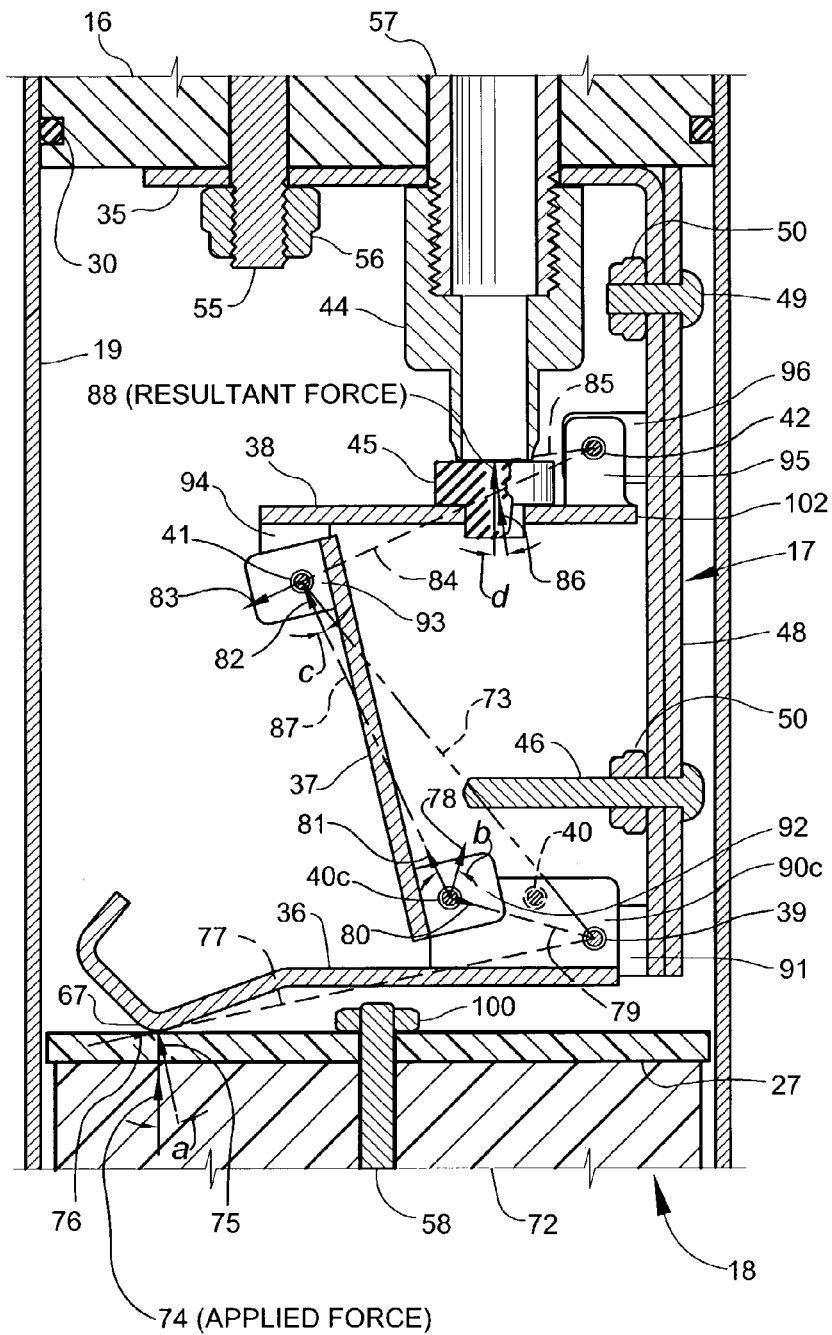
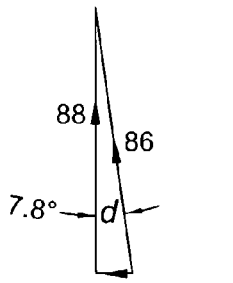
FIG. 25D
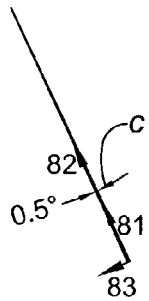
FIG. 25C
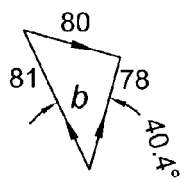
FIG. 25B
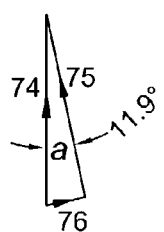
FIG. 25A
FIG. 25

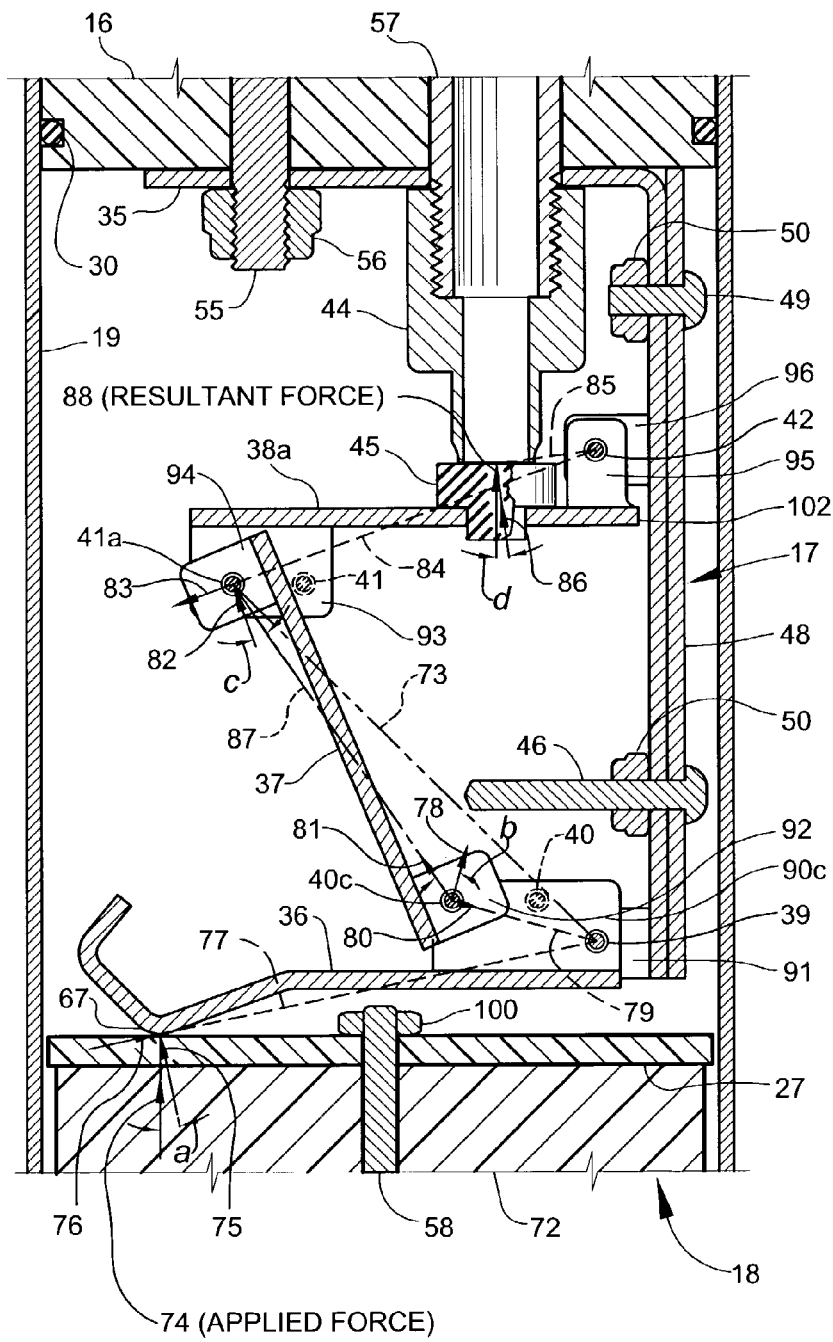
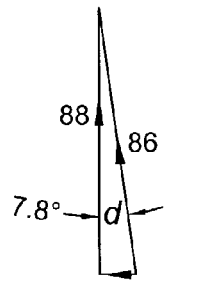
FIG. 26D
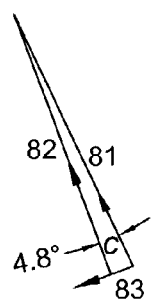
FIG. 26C
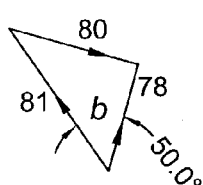
FIG. 26B
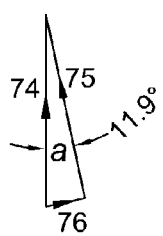
FIG. 26A
FIG. 26

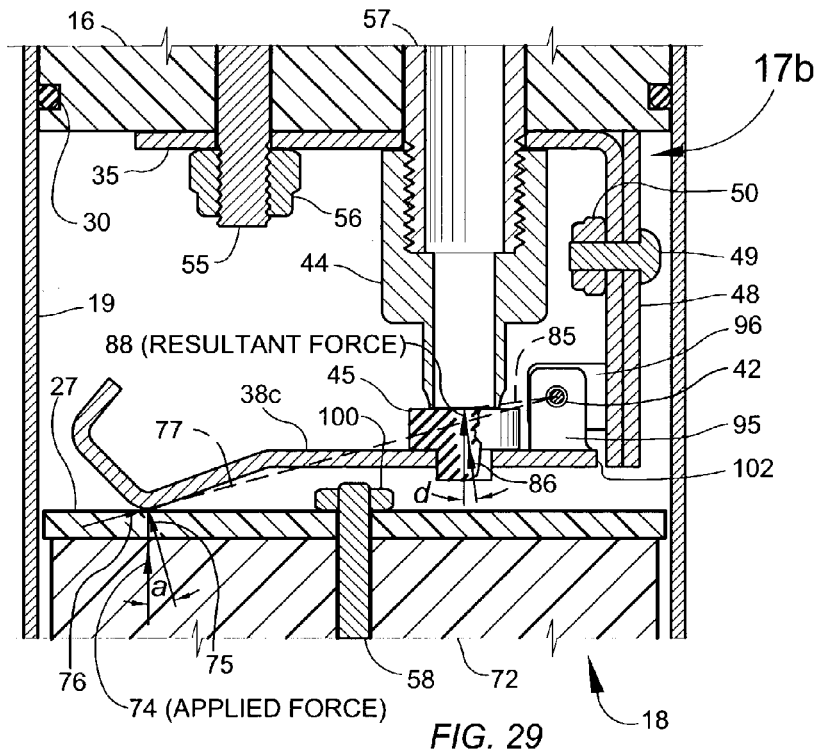
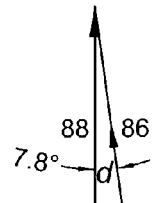
FIG. 29B
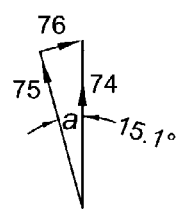
FIG. 29A
FIG. 29
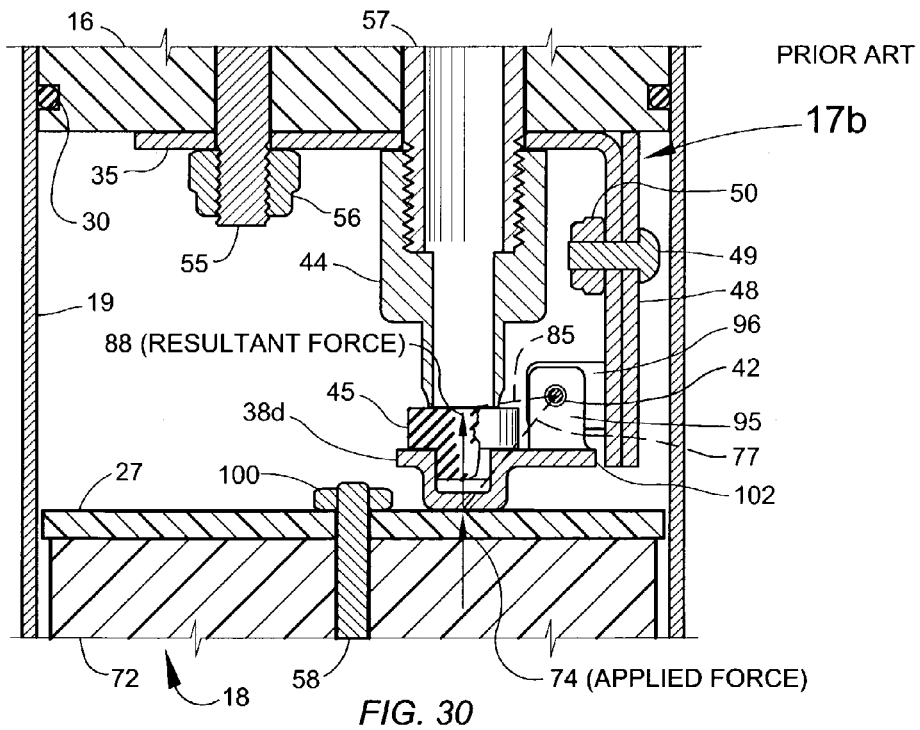
FIG. 30

RELATIONSHIP OF FORCES

LEVER-LINK-LEVER EMBODIMENTS

| FIG. | Initial Force 74 (kg-force)* | Force 75 (kg-force) | Force 78 (kg-force) | Force 81 (kg-force) | Force 82 (kg-force) | Force 86 (kg-force) | Resultant Force 88 (kg-force) |
|---|---|---|---|---|---|---|---|
| 22 | 1.00 | 0.98 | 6.07 | 18.83 | 18.43 | 59.26 | 58.71 |
| 23 | 1.00 | 0.98 | 5.09 | 9.27 | 9.17 | 29.47 | 29.20 |
| 24 | 1.00 | 0.98 | 4.46 | 22.54 | 22.12 | 70.96 | 70.31 |
| 25 | 1.00 | 0.98 | 2.91 | 3.82 | 3.82 | 12.24 | 12.13 |
| 26 | 1.00 | 0.98 | 2.91 | 4.52 | 4.50 | 17.43 | 17.27 |
| ** | 1.00 | 0.98 | 6.09 | 20.14 | 19.71 | 63.36 | 62.77 |

TWO-LEVER, SINGLE LEVER, AND PRIOR ART EMBODIMENTS

| FIG. | Initial Force 74 (kg-force) | Force 75 (kg-force) | Force 78 (kg-force) | Force 81 (kg-force) | Force 82 (kg-force) | Force 86 (kg-force) | Resultant Force 88 (kg-force) |
|---|---|---|---|---|---|---|---|
| 28 | 1.00 | 0.98 | 4.24 | None | 2.92 | 11.60 | 11.49 |
| 29 | 1.00 | 0.97 | None | None | None | 4.37 | 4.33 |
| 30 | 1.00 | None | None | None | None | None | 1.00 |

\* Any unit of force may be used to show the relationship of forces.
\*\* Lever Arm 36 has moved upwardly 1.0 degree past horizontal, thereby compressing the valve seat.

*FIG. 31*

CONSTANT-HEAD SOIL PERMEAMETER FOR DETERMINING THE HYDRAULIC CONDUCTIVITY OF EARTHEN MATERIALS AT A WIDE RANGE OF DEPTHS

RELATED INVENTION

This invention is a continuation-in-part of U.S. Utility patent application Ser. No. 09/764,375, filed Jan. 19, 2001 of Larry K. Johnson that will issue on Jun. 3, 2003 as U.S. Pat. No. 6,571,605.

BACKGROUND OF THE INVENTION

1. Field of the Invention

This invention relates to the hydraulic conductivities of liquids through permeable materials and particularly relates to the conductivity of water through earth. It also relates to testing such conductivity from the surface of the earth to great depths beneath the surface and above the water table while preventing contamination by falling soil and debris. It more particularly relates to instruments that establish a static head of water within a borehole and maintain the water at this predetermined level by use of a float and valve system. It specifically relates to a highly versatile permeameter having a float and valve system that provides a mechanical advantage enabling use of the permeameter at any selected depth up to such great depths.

2. Review of the Prior Art

It is often important to estimate the hydraulic conductivities of porous materials, such as various types of earth, for solving many agricultural, hydrological, and environmental problems. In a practical sense, these conductivities are needed in order to safely and economically develop lands for urban and agricultural uses. Hydraulic conductivity values are also important considerations in design and construction of building and roadway foundations, on site sewage wastewater treatment systems, and storm water infiltration facilities. These hydraulic conductivity values are important for design of constructed wetlands and for estimating the rate of transport of liquid contaminants from waste disposal sites and leaking storage tanks. Hydraulic conductivity values are additionally important in design of irrigation systems and drainage of agricultural lands.

Soil hydraulic conductivity can be used to describe the ability of earthen materials to transmit water. Darcy's Law describes the relationship of the volume of water, moving through a cross sectional area of soil (commonly known as flux) along the hydraulic gradient of the water flow path, to the hydraulic conductivity. Under saturated conditions, such as below a water table, hydraulic conductivity is referred to as saturated hydraulic conductivity. Even though Darcy's law was originally developed to describe saturated flow, the principles of the law can be applied to water movement in partially saturated soils above the water table.

The determination of hydraulic conductivity under field conditions can be complicated because of the natural variation of soil properties and the specific need for which the test is being conducted. Soils typically contain multiple contrasting layers and often exhibit significantly differing hydraulic conductivity values along preferential flow paths within the soil matrix.

Prior art instruments developed for measuring hydraulic conductivity of soils above the water table in the field have generally fallen into three groups. The first group introduces either a ponded static (i.e., constant) or a variable (i.e., falling) head of water into the bottom of an unlined borehole below the ground surface or into a confining ring in contact with the ground surface. Instruments that establish a static head of water within a borehole maintain the water at a predetermined level, usually by use of either a float and valve system or a marriotte tube system. The rate of water flow necessary to maintain a constant water level in the borehole at the predetermined level is utilized to estimate hydraulic conductivity of the soil.

Methods used to measure the saturated hydraulic conductivity in a borehole utilizing a constant head of water have been referred to as the shallow well pump-in technique or constant-head well permeameter. Instruments in this first group that utilize a falling head procedure usually measure the drop of water from a predetermined level in a lined or unlined borehole as it dissipates into the soil to estimate hydraulic conductivity.

The second group of instruments applies water through a semi-permeable membrane to a soil surface, which is under negative pressure (tension), to measure unsaturated hydraulic conductivity. The third group of instruments utilizes various methodologies, which include electrical resistivity procedures and gas or liquid injection into the soil through penetrating probes. The instruments in the third group typically require a power source, fluid or gas pumps, multiple chambers, borehole packers, electronic data loggers, and/or complex analysis procedures.

U.S. Pat. No. 6,212,941 of G. Cholet describes a permeameter, designed particularly for measuring the air permeability of cigarette paper, which comprises a measuring head having two chambers opening onto two sides of a test piece, one of these chambers being connected to a measuring circuit successively comprising at least one flow meter and a pumping means capable of generating pressure or a partial vacuum in the circuit, an adjusting means for maintaining the circuit at a given pressure, and an electronic circuit comprising plural calibrated amplifiers having inputs connected to the output of the flowmeter and outputs connected to the inputs of a multiplexer whose output is connected to a processor via an analog-to-digital converter.

U.S. Pat. No. 6,178,808 of X. Wang et al relates to a method for measuring hydraulic conductivity of geological samples, using a closed volume pumping system that ensures constant volume of test liquid within the sample and a shaped tube of mercury to provide a constant pressure difference across the sample for eliminating second order influences on the hydraulic conductivity measurement and to speed measurement.

U.S. Pat. No. 6,105,418 of T. Kring discloses a constant-head float valve assembly which includes a J-shaped fluid conduit for intermittently delivering water from a supply container to a borehole. As the float moves downward with dissipating water levels, a shutoff valve is contacted and thereby opened to replenish the water in the borehole. The rising water moves the float upward and away from the valve, thereby allowing pressure of the incoming water to close the valve again.

U.S. Pat. No. 6,098,448 of W. Lowry et al describes an apparatus and method for discrete soil gas and saturated liquid permeability measurements with direct push emplacement systems, such as a cone penetrometer rod. Gas or liquid is injected into the soil at a predetermined location of the penetrometer rod after such a system, having at least one injection port and at least two measurement ports, has penetrated the soil to a predetermined depth. A pressure response is recorded from each measurement port, which is at a known distance from the injection port on the same penetrometer rod, thereby providing differential pressure response data allowing calculation of the soil permeability directly by using a one-dimensional, spherical, steady-state, porous flow model to measure the effective permeability of the soil, without substantially disturbing the surrounding soil.

U.S. Pat. No. 4,561,290 of Jewell utilizes a float valve assembly, connected to a water supply reservoir, to regulate water inflow and obtain a constant water level within a borehole. The float responds to a rising water level by regulating water flow through a valve and thereby maintaining a constant water level as the water in the test bore percolates away from the bore through the soil around it at a steady rate.

U.S. Pat. No. 6,055,850 of D. Turner et al describes a multi-directional permeameter comprising a mold which is removably secured to a base and having a removably secured lid. A porous plate circumferentially disposed around the midsection of the mold and another porous plate at its bottom are connected to the interior of the mold by filter papers. The interior of the mold is filled with a soil sample to be tested. This soil sample may be selectively compressed. Water is introduced above the soil sample through an inlet port. After percolation through the soil, the filter papers, and the porous plates, the water leaves through drainage ports, whereby the coefficients of permeability of the soil sample may be determined either horizontally, vertically, or simultaneously horizontally and vertically.

U.S. Pat. No. 5,520,248 of J. Sisson et al discloses an apparatus for determining the hydraulic conductivity of an earthen material. This apparatus comprises: a) a semipermeable membrane having a fore earthen material bearing surface and an opposing rear liquid receiving surface; b) a pump connected to the semipermeable membrane rear surface and capable of delivering liquid to the membrane rear surface at a plurality of selected variable flow rates or at a plurality of selected variable pressures; c) a liquid reservoir connected to the pump and containing a liquid for pumping to the membrane rear surface; and d) a pressure sensor connected to the membrane rear surface to measure pressure of liquid delivered to the membrane by the pump which preferably comprises a pair of longitudinally opposed and aligned syringes operated so that one syringe is filled while the other is simultaneously emptied.

U.S. Pat. No. 5,161,407 of M. Ankeny et al relates to a soil desorption device and method utilizing a pressure cell which contains soil samples, the pressure cells being attachable to pneumatic pressure manifolds and selectively being independently valved. The cells may be connected to collection containers for any desorbed fluid. Each cell utilizes a cylindrical container having rubber gaskets at opposite ends thereof for sealable attachment of top and bottom plates. A thin nylon membrane having small pores is positioned at the bottom of the container, and the bottom plate has apertures, whereby fluid forced through the membrane can pass to fluid collection devices.

U.S. Pat. No. 4,984,447 of J. Phillips describes a soil testing apparatus having a hollow shaft for insertion into a test hole. The shaft includes vertically adjustable wedging blades for centering alignment in the test hole. A hand pump evacuates water from the test hole to a predetermined null point, whereupon vertical movement of a float and float rod supported and guided within the shaft over a finite period of time yields a direct percolation absorption rate.

U.S. Pat. No. 4,884,436 of M. Ankeny discloses an automated tension infiltrometer having a soil contacting base to which a porous plate is attached for interfacing the infiltrometer with the soil to be analyzed. A Marriotte column is positioned in the base so that its open bottom end abuts the porous plate, and a bubble tower is also positioned in the base with a bubbling tube operatively connecting its interior and the interior of the Marriotte column. The bubble tower is adjustable to provide variable tension to the Marriotte column. Pressure changes in the upper and lower parts of the Marriotte column are continuously measured by first and second transducers while water from the column infiltrates into the soil.

U.S. Pat. No. 4,829,817 of L. Koslowski describes an apparatus for taking soil percolation tests which comprises a threaded shaft having a plurality of marking discs that can be selectively positioned along the shaft at predetermined gradations, a positioning brace that overlies the shaft for securing the shaft in vertical alignment, a mounting disc affixed near a base end of the shaft that becomes flush with the soil when the shaft is inserted into a percolation test hole, and a receiving disc near a top end of the shaft for receiving the positioning brace as it straddles the test hole.

U.S. Pat. No. 4,561,290 of D. Jewell discloses a float valve apparatus for soil percolation measurements. This apparatus comprises a float valve assembly, integral with a water supply system, which responds to changes in a predetermined water level inside a test bore to regulate water flow through the float valve into the bore to maintain this water level. The float valve assembly is positioned at different depths below ground level by suspension at the lower end of a premarked flexible hose hanging freely inside the test bore. The float valve housing is open at its lower end so that water around it in the test bore can raise the float therewithin to throttle the water flowing down through a reducer at the end of the hose and directly above the float. After an initial transient stage, the water in the test bore percolates away from the bore through the soil around it at a steady rate.

U.S. Pat. No. 4,520,657 of H. Marthaler discloses an apparatus for determining the pressure of capillary water in soil, comprising a probe tube and a pressure measuring device that measures pressure by means of an elastically deformable membrane. The probe tube is closed and pneumatically coupled to the pressure measuring device by a pierceable and self-sealing closure member. A hollow needle suitable for piercing the closure member is attached to the pressure measuring device. Mechanical-electrical transducers measure the pressure corresponding to the deformation of the membrane.

U.S. Pat. No. 4,341,110 of P. Block relates to a percolation testing apparatus for automatically recording the rate of fluid absorption of the soil surrounding a test hole. This apparatus includes three subsystems: a) a tubular housing having a plurality of perforations at its lower end; b) a float subassembly which includes a float member, a float rod, and a channel-shaped float rod extension; and c) a clock-marker subassembly which includes a guide member for the channel extension of the float rod. During a test procedure the rate of descent of a float is recorded on a tape by a timer controlled marker.

U.S. Pat. No. 4,182,157 of R. Fink describes a soil percolation testing apparatus comprising an elongated guide rod having one end to be driven into the bottom of a test hole for supporting a rod along which a gauge rod is slidable by means of guide brackets on the gauge rod and a scale strip which is attached to the upper end of the gauge rod for vertical movement relative to a reference marker supported adjustably upon the upper portion of the guide rod. A float is connected to the lower end of the gauge rod for vertical floating movement in the test hole that moves the scale strip relative to the reference marker which is stationary on the guide rod.

In U.S. Pat. No. 3,954,612, A. Wilkerson disclosed septic tank systems buried below the ground level and having a cover to minimize rainwater soaking into its drainage bed. The gravel-filled ditch is then covered with dirt. An indicator above the ground surface shows the water level in tributaries so that excess liquid can be pumped out before upstream sewage is backed up.

In U.S. Pat. No. 3,926,143, H. Hothan describes an upright gauge that detects and gives visual indications of the presence of free water at a predetermined depth in the ground. The gauge has a tubular housing in which a spherical float, with an attached float stem, is enclosed. Water applied to the nearby soil enters the gauge, moves the float upwardly, and causes the stem to rise and signal water penetration of the soil.

In U.S. Pat. No. 3,892,126 of J. Curtin, a test hole in soil is filled with a predetermined amount of liquid and has a calibrated measuring stick extending up from a support member having a float member disposed in the liquid to indicate up and down movement of the liquid level.

In U.S. Pat. No. 2,949,766, D. Kirkham et al describe an annular water reservoir which has an inlet tube as its inner wall that enters the ground. Water is in the annular space, and a graduated cylinder that fits within the annular space is inverted and suspended by its content of air, thereby maintaining a constant pressure. As air enters the soil, the float falls accordingly.

In an article published in *Soil Science Society of America Journal*, Vol. 53, No. 5, pp. 1356–1361, Sept.–October 1989, by A. Amoozegar, entitled "A Compact Constant-Head Permeameter for Measuring Saturated Hydraulic Conductivity of the Vadose Zone", a compact constant-head permeameter is described for maintaining a constant height of water (>5 cm) at the bottom of a 4- to 10-cm-diameter hole in the unsaturated zone, and measuring the amount of water flowing into the hole, thereby measuring $K_S$ from the soil surface to a depth of two meters.

In another article published in the same issue of the same journal, pp. 1362–1367, by A. Amoozegar, entitled "Comparison of the Glover Solution with the Simultaneous-Equations Approach for Measuring Hydraulic Conductivity", the Glover solution and the simultaneous-equations approach for determining the saturated hydraulic conductivity ($K_S$) of the vadose zone by the constant-head well permeameter technique are examined. The uncertainty associated with calculating $K_S$ by the simultaneous-equations approach, as compared with using the Glover solution, is then discussed.

However, neither of these devices incorporates an apparatus for magnifying the vertical force of the float body that is necessary for valve regulation at large depths and flow volumes, nor do they incorporate a backflow check valve to prevent incident entry of suspended soil particles and other contaminates into the float chamber. In addition, neither of these devices includes a means for eliminating the entry of contaminants through its air equalizing passage into the interior of the device.

Soil hydraulic conductivity has been historically measured on a smaller scale in the laboratory, utilizing a falling or constant head of water applied to soil core samples retrieved from the field or on remolded soil samples. Laboratory centrifugal force methods are also utilized to estimate hydraulic conductivity. Laboratory measurements are often significantly at variance with in situ field measurements because of the differing methodologies and the inherent difficulty of obtaining undisturbed soil samples and replicating natural environmental and stress conditions in the laboratory.

It is desirable to have the capability to conduct hydraulic conductivity tests at any depth in earthen materials above the permanent water table. Such depths may range from zero to many meters below the ground surface. In addition, it is desirable to have adequate flow capacity for maintaining flow equilibrium in a wide range of soils. Clay and marl strata often have slow permeability, whereas sandy or gravelly soils often have high permeability and, therefore, a greater equilibrium flow rate.

Not infrequently, when clay or marl strata are at or near the surface, it is necessary to prepare a hole through such strata into underlying layers having adequate permeability for receiving septic tank fluids and the like, whereby a tract of land may be developed by building single-family homes thereon.

Another matter of developing concern is the disposal of urban area rainwater into the ground in order to maintain the water table. With such large areas in urban areas and suburban areas being covered with roofs, parking lots, sidewalks, streets, and highways, there is very little opportunity for rainwater to be absorbed into the ground. It is instead gathered into storm sewers for transport into the nearest lake, river, or ocean, thereby bypassing underground strata that are pervious enough to water to receive and transport the wasted rainwater.

Prior art inventions that utilize a float system alone do not provide a mechanical advantage ratio, thereby limiting testing to relatively shallow depths. Inventions utilizing the marriotte tube principle to establish a constant water level are also limited to relatively shallow depths of testing.

A buoyant force is provided by a float in accordance with Archimedes's Principle which states that the buoyant force on a body immersed in a fluid is equal to the weight of the fluid displaced by that body. The displacement volume of any float of practical geometric shape that can fit in a small-diameter borehole is relatively small; therefore, the depth at which such a float can provide throttling of a valve by direct buoyant force alone is limited to relatively shallow depths and small flow rates.

There is accordingly a need for an apparatus that is sufficiently rugged and versatile to measure hydraulic conductivities of soils inside a borehole at a variety of depths above the water table, ranging from shallow to deep. None of the prior art apparatuses having a float utilize a magnifying means, such as a lever arm, to increase the available force for shutting off the flow of water into the apparatus.

There is also a need for a device that can be used inside a borehole, wherein the device is subject to being struck by falling soil particles and debris, without contamination by such particles and debris through the air vent hole at its top or through water outlets at its bottom.

SUMMARY OF THE INVENTION

It is an object of the invention to provide a simple, sturdy, and versatile apparatus which functions as a constant-head soil permeameter for estimating saturated hydraulic conductivity of in situ earthen materials above the water table by establishing a constant head of water at a predetermined level in a borehole that is dug below the ground surface with ordinary hand auger equipment or with power equipment.

It is a further object to provide a constant-head soil permeameter that can, without incorporation of electronics, be effectively used to estimate hydraulic conductivity at desired test depths normally encountered above the water table and at depths much greater than the depths at which known devices that utilize a float system can be employed.

It is a still further object to provide a constant-head soil permeameter utilizing a float therewithin and leveraging principles for magnifying the upward thrust, created by the float when the water level rises within the permeameter.

It is an important object to provide principles for constructing a constant-head soil permeameter that utilizes at least one lever arm and at least one pivot for magnifying the upward thrust created by a float therewithin when the water level rises within the permeameter, whereby many variations may be constructed to meet a variety of measurement demands in the field.

It is an additional object to provide a constant-head soil permeameter that can be effectively used to determine hydraulic conductivities within a wide range of soil permeabilities.

It is also an object to provide a constant-head soil permeameter that avoids malfunction in the field by minimizing contamination from soil particles and debris falling from the side of the borehole.

It is another object to provide a constant-head soil permeameter that avoids malfunction in the field by minimizing contamination through outlets at its bottom from floating or suspended dirt and other particles in the water at the bottom of a borehole.

In accordance with these objects and the principles of the invention, the constant-head soil permeameter of this invention is an apparatus which incorporates a float, at least one lever arm, and at least one pivot that selectively increase the forces created by the float for the purpose of throttling water flow at the inlet valve.

The constant-head soil permeameter of this invention seeks to overcome disadvantages of prior art float systems by selectively multiplying the buoyant force resulting from submergence of a float alone. The permeameter increases the buoyant force by use of at least one lever arm that contacts the top of its float assembly while revolving around a fixed pivot and applying a leveraged force to the water inlet valve.

The one lever-arm embodiment, which utilizes one pivot and two pairs of lugs, has a mechanical advantage of approximately 4.3:1 at full closure, stoppers flow at a hydrostatic pressure of approximately 121 KPa and a buoyant force of 0.33 Kg-force. The float becomes almost totally submerged at this point.

The lever arm may be pivotally combined with an additional lever arm to form a compound two-lever assembly in sliding relationship while utilizing two pivots and four pairs of lugs. This embodiment has a mechanical advantage of approximately 11:1 at full closure and stoppers flow at a hydrostatic pressure of approximately 410 KPa and a buoyant force of 0.28 Kg-force.

As the preferred embodiment, the lever arm may be combined with another lever arm and an intervening link to form a compound lever-link-lever assembly, utilizing four pivots and seven pairs of lugs, which provides a mechanical advantage ratio ranging from approximately 10:1 at full valve opening up to approximately 60:1 at full valve closure at a hydrostatic pressure of approximately 410 KPa and a required buoyant force of 0.105 Kg-force. The resultant available maximum throttling force can, therefore, be approximately 60 times greater than simple buoyant force at full valve closure, depending upon the selected locations of the four pivots and the selected lengths of the lever arms and the link arm. The effective testing depth range of the permeameter is from 15 centimeters to about 30 meters. The permeability testing range of the apparatus is from $10^{-6}$ centimeters/second to $10^{-2}$ centimeters/second. The range of water flow volume through the apparatus is from zero to 2000 milliliters/minute or more at depths greater than one meter.

All of these embodiments of the constant-head soil permeameter comprises a tubular cylinder having a top end, a bottom end, means for introducing a liquid into the top end, means for selectively closing the bottom end, and means for preventing falling debris and soil from entering the top end while enabling air to flow into and out of the cylinder, the top end and the bottom end being defined in relation to usage within a vertically disposed borehole in materials permeable to the liquid, such as soil. The cylinder contains a leverage system that provides a mechanical advantage ratio for shutting off the introduction of liquid.

This leverage system comprises at least one lever arm that functions as a valve control assembly and is hereinafter thus identified. It is particularly operative when:

A) the liquid is water, the materials are earthen, and the borehole has a bottom disposed above a water table in the earthen materials; and B) the mechanical advantage ratio ranges from approximately 10:1 at full valve opening to approximately 60:1 at full valve closure.

When utilizing the lever-link-lever assembly, the valve control assembly, described hereinafter with water as the liquid, comprises the following components:

A) a valve support bracket which is longitudinally disposed and rigidly supported within the cylinder, adjacent to the inner side thereof;

B) an actuating lever arm, having a contact end and a pivot end, which is attached at the pivot end to a first pivot which is rigidly attached to the valve support bracket, the contact end resting upon the top end of a float which is axially movable within the cylinder;

C) a link, having two ends, which is attached at its lower end to a second pivot which is attached to but spaced apart by a selected distance from the first pivot; and D) a valve seat retaining lever arm, having two ends, which is pivotally attached at one end to the valve support bracket and is pivotally attached at its other end to a third pivot attached to the upper end of the link.

The top end of the cylinder comprises a top stopper, having an upper side and a lower side, which is rigidly attached to the cylinder and is encircled by an o-ring in sealing contact with the cylinder. The means for introducing water into the top end of the cylinder comprises a reservoir for containing water which is disposed on the surface of the ground, a hose connection which is rigidly attached to the top stopper and projects outwardly from its upper side and has a bore therewithin, a hose for connecting the reservoir to the hose connection, and a valve body which is rigidly attached to the lower side of the stopper and has a bore therewithin in fluid communication with the bore within the hose connection.

The valve seat retaining lever arm comprises a valve seat which is attached thereto in facing relationship to the valve body and is adapted for selectively shutting off the introducing of water into the cylinder from the reservoir.

The cylinder additionally contains a buoyant float body that is axially movable within the cylinder and has upper and lower surfaces. The upper surface exerts pressure against the contact end of the actuating lever arm when the float is supported by water within the cylinder.

The constant-head soil permeameter may be described as comprising the following lever-link-lever assembly within its cylinder which provides a mechanical advantage ratio:

A) a valve support bracket, rigidly attached to the top stopper, having an upper pair and a lower pair of spaced-apart lugs attached perpendicularly thereto and projecting toward the center of the cylinder;

B) an actuating lever arm, comprising a contact end and a pivot end, having one pair of spaced-apart lugs attached perpendicularly thereto at its pivot end and projecting upwardly, being attached to the lower pair by a first pivot;

C) a link having upper and lower ends and a pair of spaced-apart lugs attached perpendicularly thereto at each end thereof which project toward the valve support bracket, the pair at the lower end being attached by a second pivot to the pair of spaced-apart lugs on the pivot end of the actuating lever arm, the second pivot being spaced from the first pivot by a selected distance; and D) a valve seat retaining lever arm having two pairs of spaced-apart lugs attached perpendicularly thereto at the ends thereof and projecting in opposite directions, one pair being pivotally attached to the pair of spaced-apart lugs on the upper end of the link by a third pivot and the other pair of lugs being pivotally attached to the upper pair of lugs on the valve support bracket.

The means for preventing falling debris and soil from entering the top end of the cylinder while enabling air to flow into and out of the cylinder comprises an inverted J-shaped tube, having a long portion which passes through the stopper and a short portion having a filter screen at its outer end, the filter screen being disposed to face toward the upper side of the stopper and being spaced from the upper side. The short portion is downwardly enlarged, whereby falling debris and soil is dispersed outwardly and a clear space is left beneath the screen.

The means for selectively closing the bottom end of the cylinder comprises a bottom stopper, having an upper surface and a lower surface, which is rigidly attached to the cylinder, an o-ring encircling the stopper and in sealing contact with the cylinder, an axially disposed bolt attached to the stopper and extending upwardly beyond its upper surface, at least one longitudinally disposed hole extending through the bottom stopper, and a check valve disposed beneath the lower surface, whereby reverse flow of water from the borehole toward the stopper lifts the check valve and closes the hole and the bottom end.

This constant-head soil permeameter, adapted for operational use within a borehole in earthen materials, comprises a cylindrical housing having a top end and a bottom end which has a flow-through means for allowing water entering the top end to form a first water level within the housing and then to flow through the bottom end into the borehole to form a second water level therewithin when the second water level is lower than the first water level and having a closing means for preventing water from flowing into the cylindrical housing when the second water level is higher than the first water level.

This flow-through means comprises a bottom stopper which is rigidly attached to the cylindrical housing, has a countersunk bottom surface forming a downwardly extending skirt that contacts the bottom of the borehole when the permeameter is resting thereupon, has at least one longitudinally disposed hole through the stopper, and has at least one laterally extending hole through the skirt.

This closing means comprises a check valve guide which is axially and rigidly attached to the countersunk bottom surface of the stopper, a disk-shaped check valve which is loosely and axially fitted to the check valve guide, and a disk-shaped baffle, having a plurality of longitudinally disposed holes therethrough, which is rigidly and perpendicularly attached to the check valve guide and disposed beneath the check valve, whereby backflow of water from the borehole toward the bottom stopper passes through the plurality of holes in the baffle and lifts the check valve to block the at least one longitudinally disposed hole in the bottom stopper.

The method of using the permeameter of the invention is as follows:

1) The rate of water flow into the borehole that is necessary to maintain the constant head is recorded at appropriate intervals during the test period; and 2) The information recorded during the test, which also includes height of constant water column, rate of flow, and borehole geometry, is factored into an appropriate mathematical equation to provide an estimate of hydraulic conductivity.

BRIEF DESCRIPTION OF THE DRAWINGS

FIG. 22 is a sectional view of the middle part of the constant-head soil permeameter, as the preferred embodiment of this invention, showing the valve control assembly in its fully closed position as in FIG. 8, including applied forces, resultant forces, and angles therebetween.

FIG. 22A is a force diagram which resolves the vertically aligned applied force, at the point of application thereof by the float assembly onto the heel of the actuating lever arm, into a force along the first imaginary line of action between the point of application to the axis of the first pivot and a force aligned perpendicularly thereto.

FIG. 22B is a force diagram which resolves the force resulting from the torque produced at the second pivot, exerted perpendicularly to a second imaginary line of action between the first and second pivots, into a force aligned with this second line of action and a force aligned with a third imaginary line of action connecting the second and third pivots.

FIG. 22C is a force diagram which resolves the force aligned with this second line of action, when applied to the third pivot connecting the link and the valve retaining lever arm, into a force applied perpendicularly to a fourth imaginary line of action between the third pivot and the fourth pivot, which connects the valve retaining lever arm to the valve support bracket, and a force aligned with this fourth imaginary line of action.

FIG. 22D is a force diagram which resolves the force applied at the center of the valve seat, as the valve seat retaining arm revolves around the fourth pivot and multiplies the force applied perpendicularly to the fourth imaginary line of action by the ratio of the length of the fourth imaginary line of action to the length of a fifth imaginary line of action between the fourth pivot and the center of the valve seat, into a force aligned with this fifth imaginary line of action and a resultant force which is aligned vertically.

FIG. 23 is a sectional view of the middle part of the constant-head soil permeameter, as a second embodiment of this invention having its second pivot displaced a short distance away from the valve support bracket and approximately in parallel with the first imaginary line of action, showing the valve control assembly in its fully closed position as in FIG. 8, including applied forces, resultant forces, and angles therebetween.

FIG. 23A is a force diagram which resolves the vertically aligned applied force in the same manner as for FIG. 22A.

FIG. 23B is a force diagram which resolves the force resulting from the torque produced at the displaced second pivot in the same manner as for FIG. 22B.

FIG. 23C is a force diagram which resolves the force aligned with this second line of action in the same manner as for FIG. 22C.

FIG. 23D is a force diagram which resolves the force applied at the center of the valve seat in the same manner as for FIG. 22D.

FIG. 24 is a sectional view of the middle part of the constant-head soil permeameter, as a third useful embodiment of this invention having its second pivot displaced a relatively large distance away and upwardly from the valve support bracket, showing the valve control assembly in its fully open position as in FIG. 8, including applied forces, resultant forces, and angles therebetween.

FIG. 24A is a force diagram which resolves the vertically aligned applied force in the same manner as for FIG. 22A.

FIG. 24B is a force diagram which resolves the force resulting from the torque produced at the displaced second pivot in the same manner as for FIG. 22B.

FIG. 24C is a force diagram which resolves the force aligned with this second line of action in the same manner as for FIG. 22C.

FIG. 24D is a force diagram which resolves the force applied at the center of the valve seat in the same manner as for FIG. 22D.

FIG. 25 is a sectional view of the middle part of the constant-head soil permeameter, as a fourth useful embodiment of this invention having its second pivot displaced a relatively large distance away from the valve support bracket, showing the valve control assembly in its fully closed position as in FIG. 8, including applied forces, resultant forces, and angles therebetween.

FIG. 25A is a force diagram which resolves the vertically aligned applied force in the same manner as for FIG. 22A.

FIG. 25B is a force diagram which resolves the force resulting from the torque produced at the second pivot in same manner as for FIG. 22B.

FIG. 25C is a force diagram which resolves the force aligned with this second line of action in the same manner as for FIG. 22C.

FIG. 25D is a force diagram which resolves the force applied at the center of the valve seat in the same manner as for FIG. 22D.

FIG. 26 is a sectional view of the middle part of the constant-head soil permeameter, as a fifth useful embodiment of this invention having its second pivot in the same position as in FIG. 25 and its third pivot displaced a medium distance away from the valve support bracket, showing the valve control assembly in its fully closed position as in FIG. 8, including applied forces, resultant forces, and angles therebetween.

FIG. 26A is a force diagram which resolves the vertically aligned applied force in the same manner as for FIG. 22A.

FIG. 26B is a force diagram which resolves the force resulting from the torque produced at the second pivot in same manner as for FIG. 22B.

FIG. 26C is a force diagram which resolves the force aligned with this second line of action in the same manner as for FIG. 22C.

FIG. 26D is a force diagram which resolves the force applied at the center of the valve seat in the same manner as for FIG. 22D.

FIG. 29 is a sectional view of the middle part of a greatly simplified embodiment of the constant-head soil permeameter, showing a single lever arm as the valve control means in its fully closed position.

FIG. 29A is a force diagram which resolves the vertically aligned applied force, exerted upon the heel of the lever arm by the rising top of the float, into a force aligned with an imaginary line of action, between this line of contact and the center of the single pivot, and a force which is aligned perpendicularly thereto.

FIG. 29B is a force diagram which resolves the force aligned perpendicularly to a third imaginary line of action, between the center of the single pivot and the center of the valve body, into a force aligned with this line of action and the resultant force which is aligned vertically at the center of the valve body.

FIG. 30 is a sectional view of the middle portion of the soil permeameter, with a greatly modified valve seat retaining lever arm in order to simulate the prior art in which no leverage is used.

FIG. 31 shows two tables, the upper table providing six calculated forces for each of five embodiments of the invention, identified by figure numbers, and for the instance (identified by **) when the actuating lever arm has moved one degree upwardly after closing the valve, as it compresses the neoprene valve body, and the lower table providing the same calculated forces, where applicable, for the two-lever, single lever, and prior art embodiments.

DETAILED DESCRIPTION OF THE PREFERRED EMBODIMENTS

FIGS. 1–21 are drawings from the parent application that describe the preferred embodiment, having two lever arms and a connecting link, referred to as the lever-link-lever embodiment. FIGS. 22–30 are drawings that show additional embodiments, including a prior art embodiment for comparative purposes, illustrating the versatility and broad usefulness of the invention. FIGS. 31–34 are tables, illustrative drawings, and graphs that provide information enabling the embodiments to be compared with each other and with the prior art.

Figure 1:
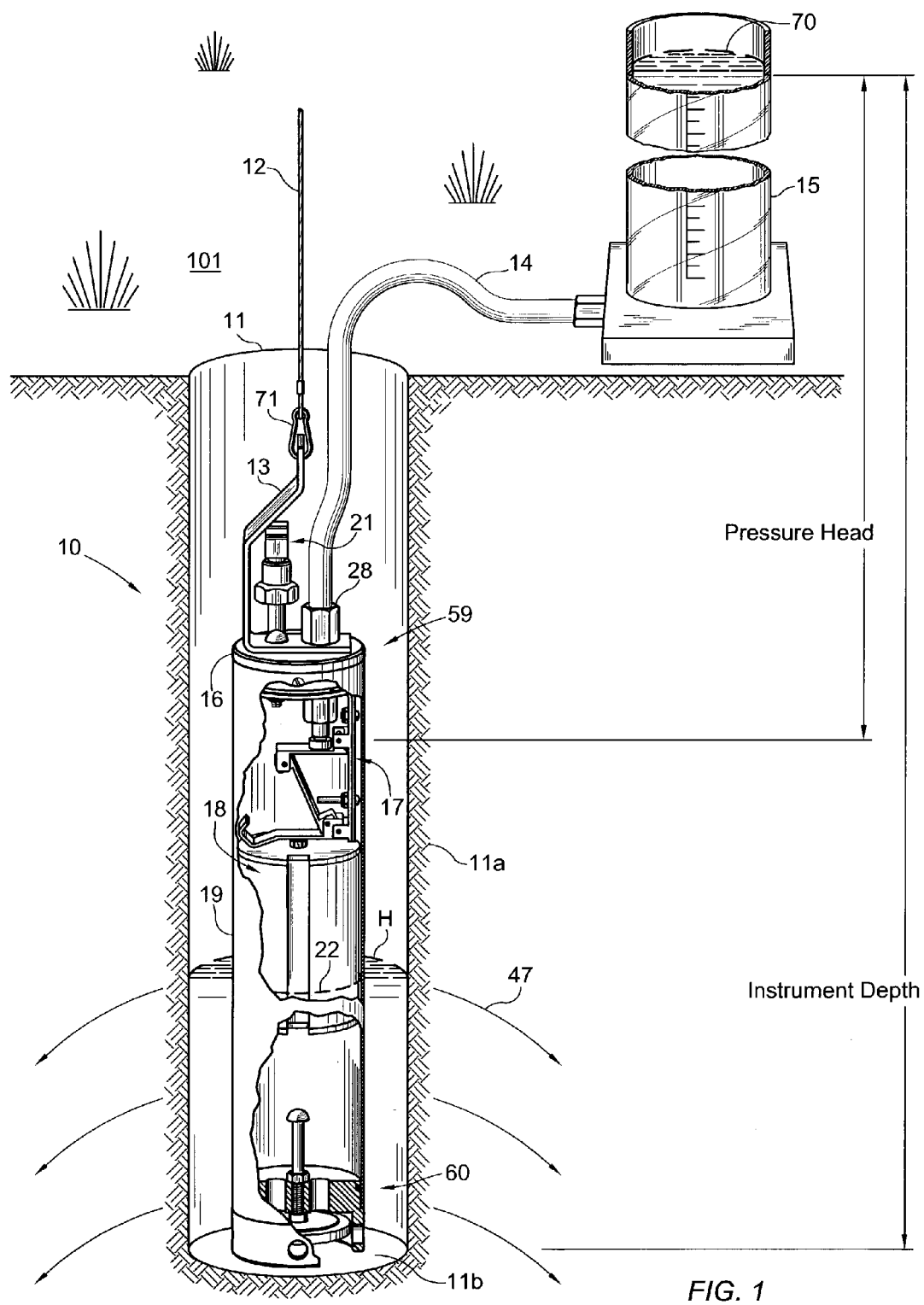
FIG. 1 is an isometric and partial cutout view of the preferred embodiment of the constant-head soil permeameter in place in a shallow borehole dug in earthen materials.

As shown in FIG. 1, constant-head soil permeameter 10 of this invention comprises cylindrical housing 19, means 21 for venting air from housing 19 and preventing dirt from entering the top of housing 19, means 17 for providing a mechanical advantage ratio for shutting off water flow into housing 19, and means 60 for preventing debris and fallen earth particles from entering the bottom of housing 19. More specifically, valve control assembly 17, float assembly 18, base assembly 60, and portions of the flow control assembly are inside of housing 19.

Permeameter 10 also comprises suspension bracket 13 and utilizes a lifting and/or support means connected thereto. Cable 12 has snap connection 71 at its lower end which is secured through hole 99 in bracket 13 and is attached at its upper end to any suitable anchoring mechanism above ground surface 101. Permeameter 10 is connected to calibrated reservoir 15, which is disposed on ground surface 101 near borehole 11, by hose 14 which is attached to hose connection 28 at its lower end. Hose 14 has a suitable length for the testing depth. Hose connection 28, as a part of flow control assembly 59, provides the entry port for water into housing 19 during tests.

Housing 19 consists of a tubular cylinder suitable for isolation and protection of interior components of the permeameter. Permeameter 10 may rest on bottom 11b of borehole 11 or may be supported at any desired height above bottom 11b by cable 12.

Top stopper 16, as shown in FIGS. 2, 4, 5, and 6, provides a rigid mounting base for valve control assembly 17, suspension bracket 13, filter vent assembly 21, and hose connection 28. Top stopper 16 incorporates an o-ring 30 to provide a seal between stopper 16 and housing 19, thereby preventing soil particles and debris from entering the invention in the annular space between top stopper 16 and housing 19.

Figure 2:
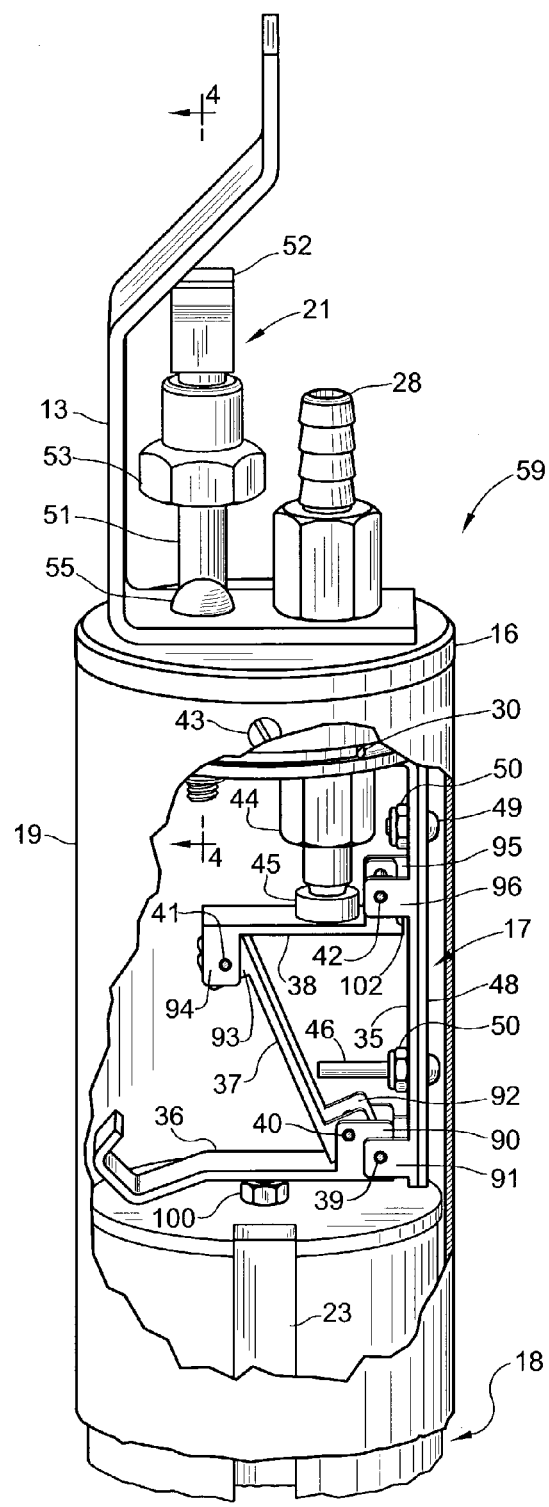
FIG. 2 is an isometric and partial cutout view of the upper part of the soil permeameter shown in FIG. 1, showing the top stopper, the valve control assembly in its fully closed position, and a portion of the float valve assembly.
Figure 16:
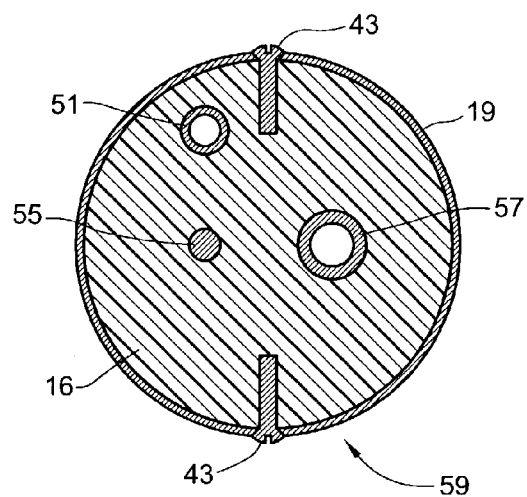
FIG. 16 is a sectional view of the top stopper, taken along line 16—16 in FIG. 6, of the constant-head soil permeameter.
Figure 18:
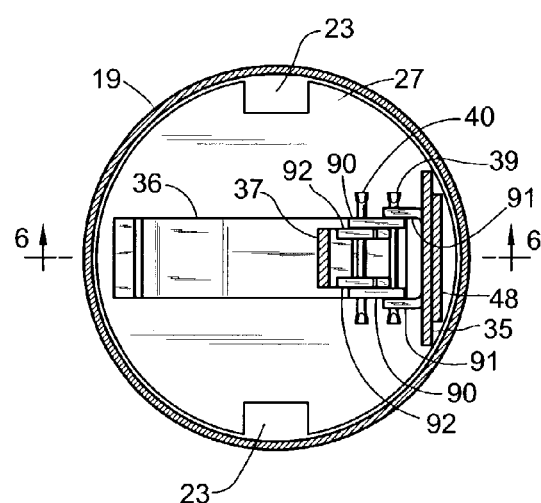
FIG. 18, taken along the line 18—18 in FIG. 6, is a top view of the actuating lever arm, the three lug pairs, the two lower pivots, and the upper float guide of the float assembly, plus cross sections of the valve support bracket, the stabilizing bracket, and the link, the relative distances apart of the three lug pairs also being isometrically illustrated in FIG. 2.

Hose connection 28 and valve body 44 are hydraulically connected and secured through top stopper 16 by commercial pipe 57, as shown in FIGS. 5, 6, 7, and 16. Suspension bracket 13 and valve control assembly 17 are additionally secured to top stopper 16 by commercial bolt 55 and commercial nut 56. Top stopper 16 is secured to housing 19 by commercial machine screws 43, as seen in FIGS. 2 and 16.

Filter vent assembly 21, as shown in FIGS. 2, 4, 5, 6, and 13, comprises commercial pipe nipple 51, commercial pipe elbows 52, filter housing 53, filter screen 31, and filter retaining snap ring 54. Pipe nipple 51 is threadably fastened to top stopper 16 in a manner that allows free movement of air through vent pathway 68 in filter vent assembly 21 and top stopper 16. Filter vent assembly 21 is constructed as an inverted J-shape to discourage entry of soil particles into the cylinder chamber through gravitational action while allowing free passage of atmospheric gas and excluding soil particles and other debris. Because filter screen 31 faces downwardly and is spaced from the upper side of stopper 16, there is substantially no opportunity for soil and debris to pass through screen 31 into vent pathway 68, whereby contamination of the apparatus is substantially impossible.

Valve control assembly 17, as shown in FIGS. 2, 5, 6, 7, and 8, comprises valve body 44, valve seat 45, valve seat retaining lever arm 38, valve support bracket 35, stabilizing bracket 48, link 37, and actuating lever arm 36. Valve support bracket 35 and stabilizing bracket 48 are fastened together by commercial bolts 49 and 46 and by commercial nuts 50. Stop heel 102 at the pivot end of lever arm 38, by contacting bracket 35, prevents arm 38 from dropping too far and thereby prevents heel 67 on lever arm 36 from moving to the right beyond the center of nut 100.

Valve support bracket 35, actuating lever arm 36, link 37, and valve seat retaining lever arm 38 comprise pairs of spaced apart and perpendicularly extending support lugs, shown in FIGS. 2, 5, 6, 7, and 8. Each lug pair 90, 91, 92, 93, 94, 95, 96 has a hole drilled completely through both lugs, and a pivot 39, 40, 41, 42 is inserted completely through each drilled hole of the lug pairs, thereby serving as an axis of rotation. The pivots are crimped on the outsides of the lugs to ensure retention. These pivots are parallel to each other and provide a nearly frictionless connection between actuating lever 36, link 37, valve seat retaining lever arm 38, and stationary valve support bracket 35.

The pivots allow actuating lever arm 36, link 37, and valve seat retaining lever arm 38 to move freely in a plane parallel to the longitudinal axis of stationary valve support bracket 35.

Actuating lever arm 36, which comprises a single lug pair 90, revolves around pivot 39, which is also connected to lug pair 91 that is rigidly attached to valve support bracket 35. Link 37, which comprises two lug pairs 92 and 93 extending in opposite directions, is connected at pivot 40 to actuating lever arm 36 and at pivot 41 to valve retaining lever arm 38. Link 37 revolves around both pivots 40 and 41 in response to the rising and lowering of float assembly 18. Valve seat retaining lever arm 38, which comprises two lug pairs 94 and 95 extending in opposite directions, revolves around pivot 42 which is also connected to lug pair 96 that is rigidly attached to valve support bracket 35.

Valve support bracket 35 provides a rigid stationary connection between valve seat retaining lever arm 38 and actuating lever arm 36. Link 37 provides a movable rigid connection between valve seat retaining lever arm 38 and actuating lever arm 36. Valve control assembly 17 is shown in a fully opened position in FIG. 5 and in a fully closed position in FIGS. 2 and 6.

Figure 11:
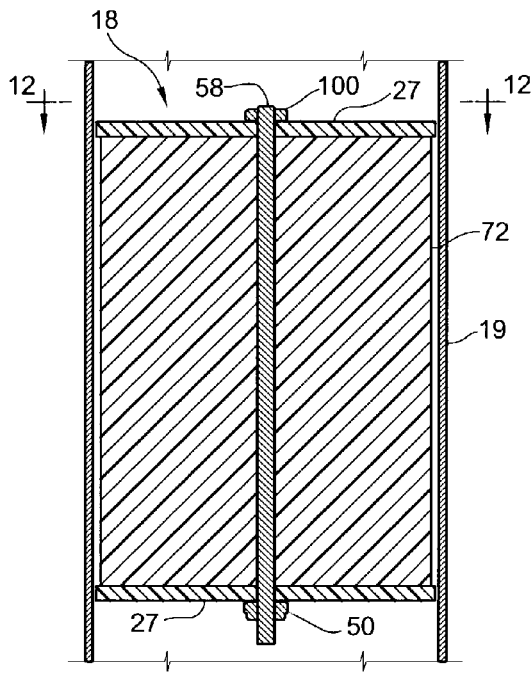
FIG. 11 is a sectional view of the buoyant float body and the surrounding cylindrical housing of the constant-head soil permeameter.
Figure 12:
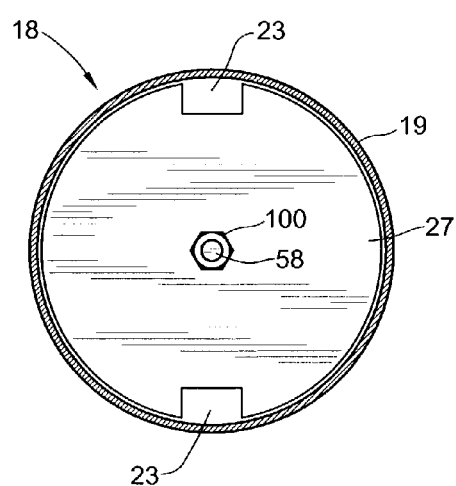
FIG. 12 is a plan view of the float assembly, taken along line 12—12 in FIG. 11, and a sectional view of the surrounding cylindrical housing of the constant-head soil permeameter.
Figure 13:
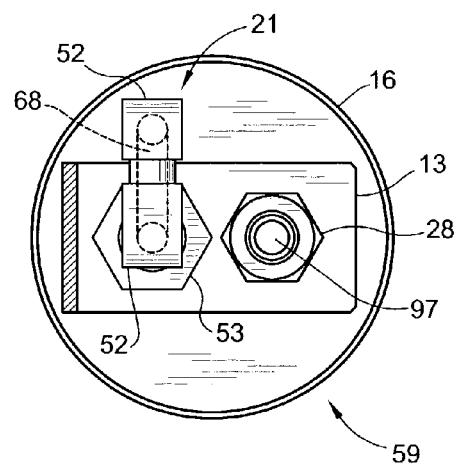
FIG. 13 is a plan view of the filter vent assembly and hose connection at the top end of the cylinder and a partial sectional view of the suspension bracket, taken along line 13—13 in FIG. 5.
Figure 14:
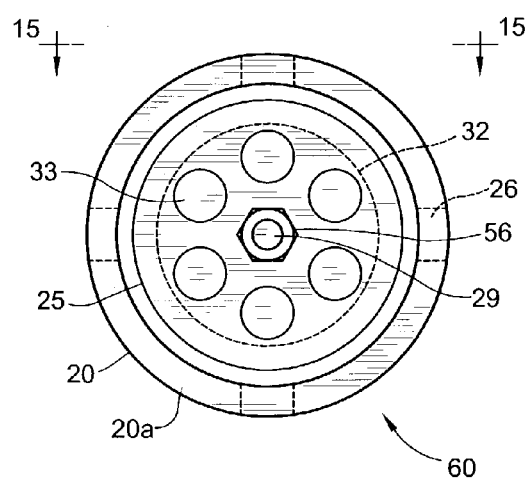
FIG. 14 is a bottom view of the base assembly, taken along line 14—14 in FIG. 10, of the constant-head soil permeameter.
Figure 15:
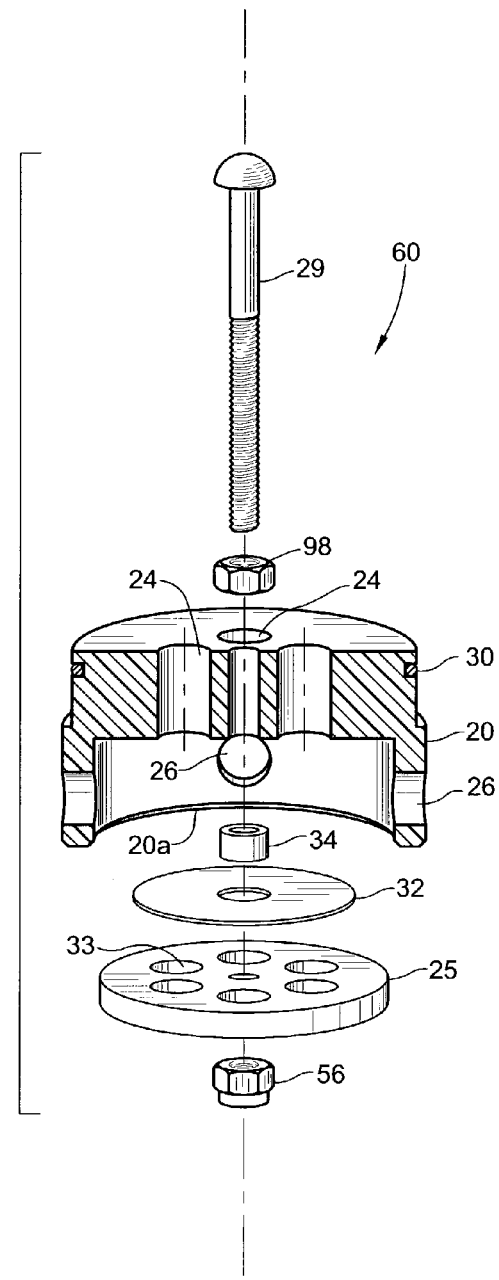
FIG. 15 is an isometric and partial sectional exploded view of the base assembly, taken generally along line 15—15 in FIG. 14.

Float assembly 18, as shown in FIGS. 11 and 12, comprises buoyant float body 72, upper and lower float end guides 27, commercial threaded rod 58 and commercial nuts 50 and 100. Water flow channels 23 are disposed opposite to each other on the perimeter of float body 72 and extend longitudinally through float body 72 and both float end guides 27, as seen in FIGS. 11 and 12.

Figure 17:
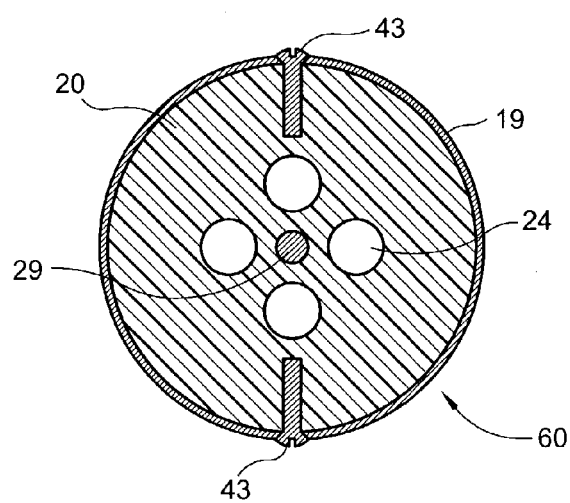
FIG. 17 is a sectional view, looking upwardly, of the base assembly of the soil permeameter, taken along line 17—17 in FIG. 9.
Figure 19:
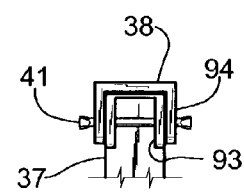
FIG. 19, taken along the line 19—19 in FIG. 6, is a sectional side view of the third pivot, both pairs of lugs which rotate around it, and the valve seat retaining lever arm, as well as a side view of the upper portion of the link.

Base assembly 60, as shown in FIGS. 3, 9, 10, 14, and 15, comprises bottom stopper 20 which provides a rigid mounting body for o-ring 30 which is in sealing contact with housing 19, commercial bolt 29, check valve 32, check valve guide 34, baffle 25, longitudinally disposed holes 24 through stopper 20, laterally disposed holes 26 in the skirt of bottom stopper 20, and commercial nuts 56 and 98. Check valve 32 moves freely in a vertical direction on check valve guide 34. Bottom stopper 20 is secured to housing 19 by commercial machine screws 43, as shown in FIG. 17.

Figure 9:
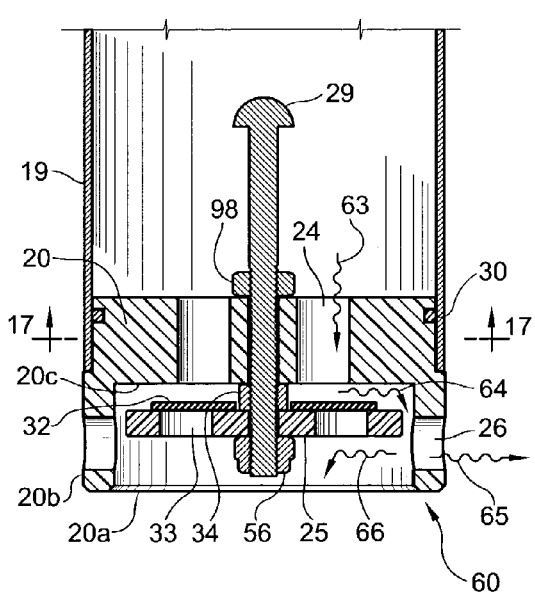
FIG. 9 is a sectional view of the lower part of the soil permeameter showing the base assembly and its check valve in its fully opened position, with flow arrows indicating the flow of water from the interior of the cylinder into the borehole.
Figure 10:
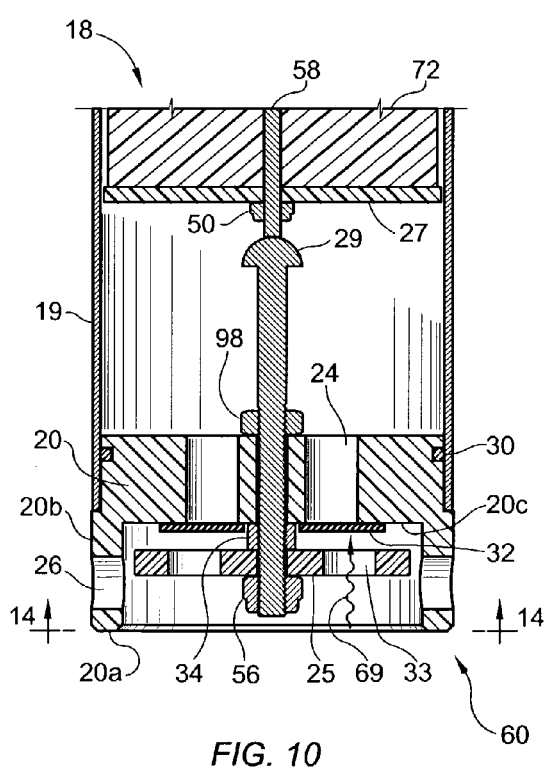
FIG. 10 is a sectional view of the lower part of the soil permeameter, showing the base assembly and its check valve in its fully closed position and with the buoyant float body in a lowered position, in contact with a bolt attached to the base assembly, as a flow arrow indicates attempted movement of water from the borehole toward the interior of the cylinder.

Check valve 32 rests on baffle 25 and remains open during normal operation, as illustrated in FIG. 9, when water is flowing through base assembly 60 to borehole 11. However, check valve 32 rises into contact with countersunk bottom surface 20c and closes holes 24 to prevent backflow, as seen in FIG. 10, if forced upward by reverse water flow, shown by flow arrow 69 through hole 33 in baffle 25.

Valve control assembly 17 and float assembly 18 provide flow control of water from reservoir 15 to maintain a constant head of water in borehole 11. This constant head of water is established by the preset level of the permeameter within borehole 11 and the resultant equilibrium of the pressure head induced by the height of water 70 in reservoir 15 and the rate of water absorption 47 into earthen material 11a, as depicted in FIG. 1. The force provided by any float assembly to effectively stop or throttle the flow through a valve must be sufficient to exceed hydrostatic pressures produced by the height of water 70 through hose column 14 and resultant pressure of water flow at control valve components 44 and 45 in the constant-head soil permeameter.

Figure 32:
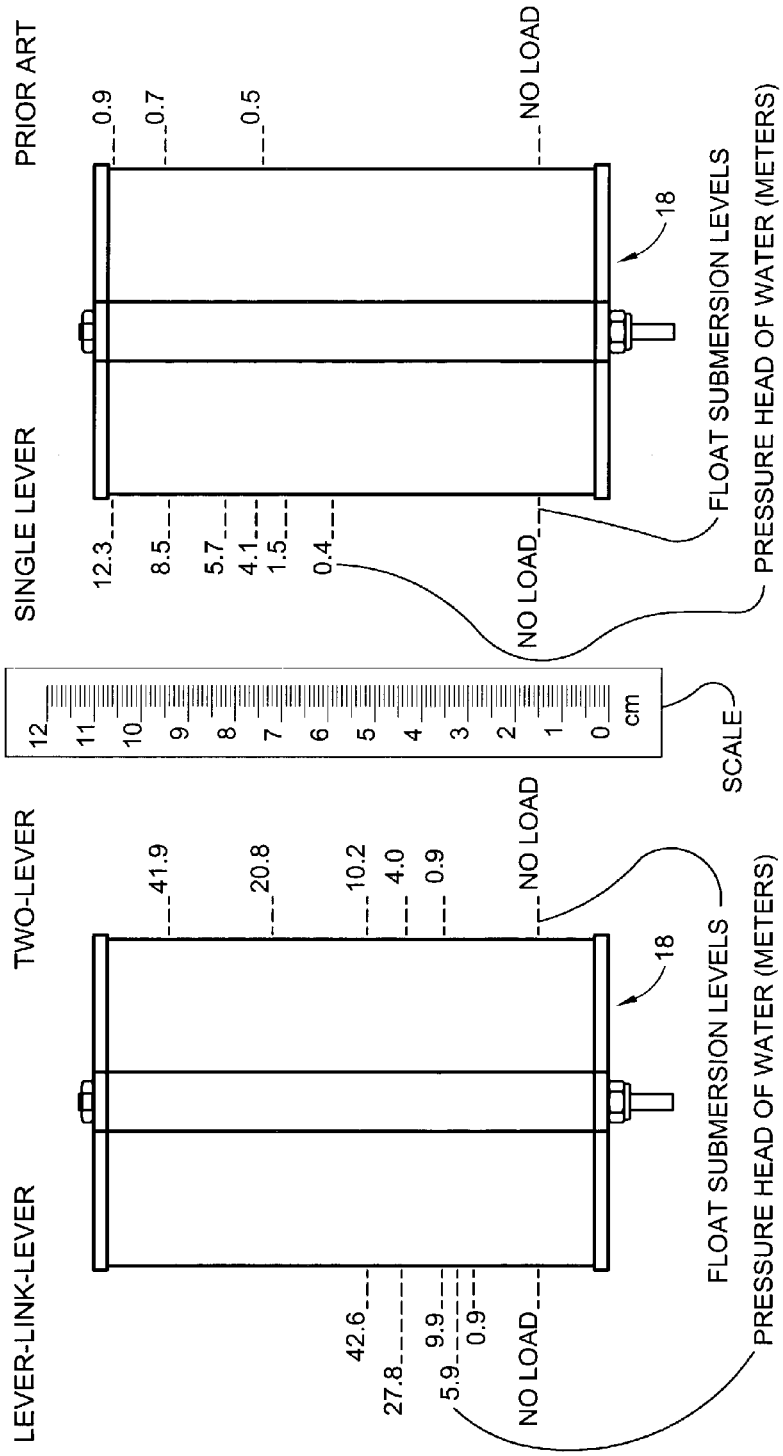
FIG. 32 shows two drawings of the float body used in all embodiments of the invention, as well as in FIG. 30 that illustrates prior art forces, to illustrate the float submersion required to stopper the valve at various pressure heads of water for the lever-link-lever and for the two-lever embodiments (left float), and for the single lever and prior art embodiments (right float) as the float bodies are submerged in surrounding water within the cylindrical housing, with depths of float submergence and corresponding borehole depths being given for each float.

As the depth of testing increases, the increasing hydrostatic pressure at control valve components 44 and 45 of valve control assembly 17 requires progressively greater water displacement by float assembly 18 to throttle and maintain flow equilibrium. Other constant head devices utilizing a float alone with a float displacement equivalent to displacement of float assembly 18 become fully submerged and, therefore, ineffective at deep depths, as illustrated in FIG. 32. Indeed, prior art devices become fully submerged at a depth of one meter. In addition, the float assemblies of other constant-head devices, not having a mechanical advantage means, displace a greater volume of water than the present invention at any given depth while maintaining equilibrium, thereby causing a correspondingly greater transient rise of the water level, H, within the borehole. This complicates determining the constant height of water for permeability test determinations.

The entire constant-head soil permeameter of this invention is constructed of stainless steel except for: a) o-rings 30, check valve 32, and valve seat 45 which are made of neoprene; b) top stopper 16, bottom stopper 20, baffle 25, and upper and lower float end guides 27 which are made of polycarbonate plastic; and c) float 72 which is made of a closed-cell foamed plastic.

Explanation of Forces Exerted Within Valve Control Assembly 17

The mechanical advantage ratio that is necessary for hydraulic testing at considerable depths is provided by the lever-link-lever action of valve control assembly 17. A force along a line of action is required to make any body rotate about an axis. The perpendicular distance from the line of action of the force to the axis of rotation is the moment arm of the force and the product of the force and the moment arm of the force is the torque.

As seen in FIGS. 7, 8, 22, 22A, 22B, 22C, and 22D, buoyant or applied force 74, which has a line of action parallel to the longitudinal axis of valve support bracket 35, can be resolved into force components 75 and 76, which are, respectively, perpendicular and parallel to imaginary line 77 which joins the point of application of force 74 to the axis of actuating lever arm 36, as illustrated in FIG. 22A. Line 77 is, therefore, a moment arm of force 75 about pivot 39. The torque applied at pivot 39 is equal to the product of force 75 and the length of moment arm 77. Force 76 is directed toward the axis at pivot 39 and does not cause rotation.

As actuating lever arm 36 revolves around pivot 39, every point on actuating lever arm 36, including pivot 40 on lugs 90, sweeps out the same angle at any time. The torque produced at pivot 39 from force 75 results in force 78 at pivot 40, which acts in a line of action perpendicular to moment arm 79. Force 78 is proportional to the ratio of the length of moment arm 77 to the shorter length of moment arm 79, thereby greatly exceeding force 75. Force 78 can be resolved into force 81 and force 80 along moment arm 79, as illustrated in FIG. 22B.

Force 81 lies along line of action 87, which is an imaginary line connecting pivot 40 and pivot 41 of link 37, all parts of which act as a rigid plate. Force 80 is directed toward pivot 39 and does not cause rotation. Forces 81 and 80 can be determined by two-dimensional equilibrium equations. The maximum ratio of force 81 to force 78 is achieved just before pivot 40 and line of action 87 of force 81 move across line 73. Line of action 87, however, is prevented from crossing line 73 by bolt 46, which limits the rotational travel of link 37.

Force 81 can be resolved into force components 82 and 83 which are, respectively, perpendicular and parallel to imaginary line 84 which joins the point of application of force 81 at pivot 41 with pivot 42, as illustrated in FIG. 22C. All parts of valve retaining lever arm 38, similarly to link 37 and actuating lever arm 36, act as a rigid plate. Line 84 is, therefore, a moment arm of force 82 about the axis of pivot 42.

Figure 7:
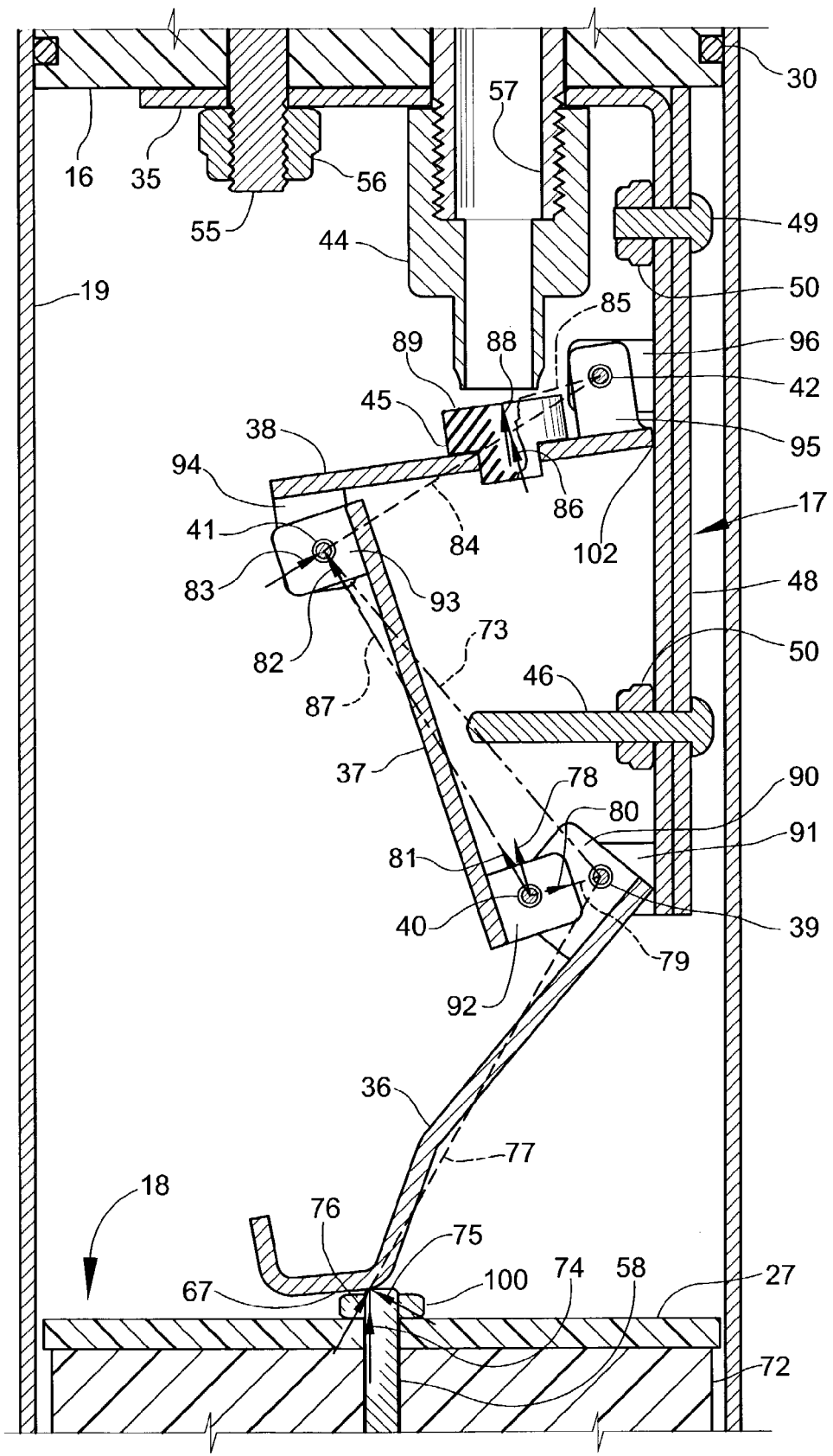
FIG. 7 is an enlarged sectional view of the middle part of the constant-head soil permeameter showing the same components as in FIGS. 5 and 6 with the valve control assembly in its fully opened position, and illustrating the force components acting at their respective pivots and the imaginary lines of action connecting the pivots.

The torque applied at pivot 42 is equal to the product of force 82 and the length of moment arm 84. Force 83 is directed either toward or away from the axis at pivot 42, depending on the degree of closure of valve control assembly 17, and does not cause rotation in either case. Force component 82 is nearly superimposed on line of force 87, as seen in FIG. 7, because this line of force is nearly perpendicular to moment arm 84 at the fully open position.

As valve seat retaining lever arm 38 revolves around pivot 42, every point on valve retaining lever arm 38, including valve seat 45, sweeps out the same angle at any time. Force 86 is perpendicular to moment arm 85 and is a result of the torque at pivot 42 acting along the length of moment arm 85. Force 86 is proportional to the ratio of the length of moment arm 84 to the shorter length of moment arm 85, thereby greatly exceeding force 82 which applies the initial torque. Force 86 can be resolved into component force 88 that is perpendicular to face 89 of valve seat 45 and another force (neither shown nor numbered) that is parallel thereto, as illustrated in FIG. 22D.

Figure 8:
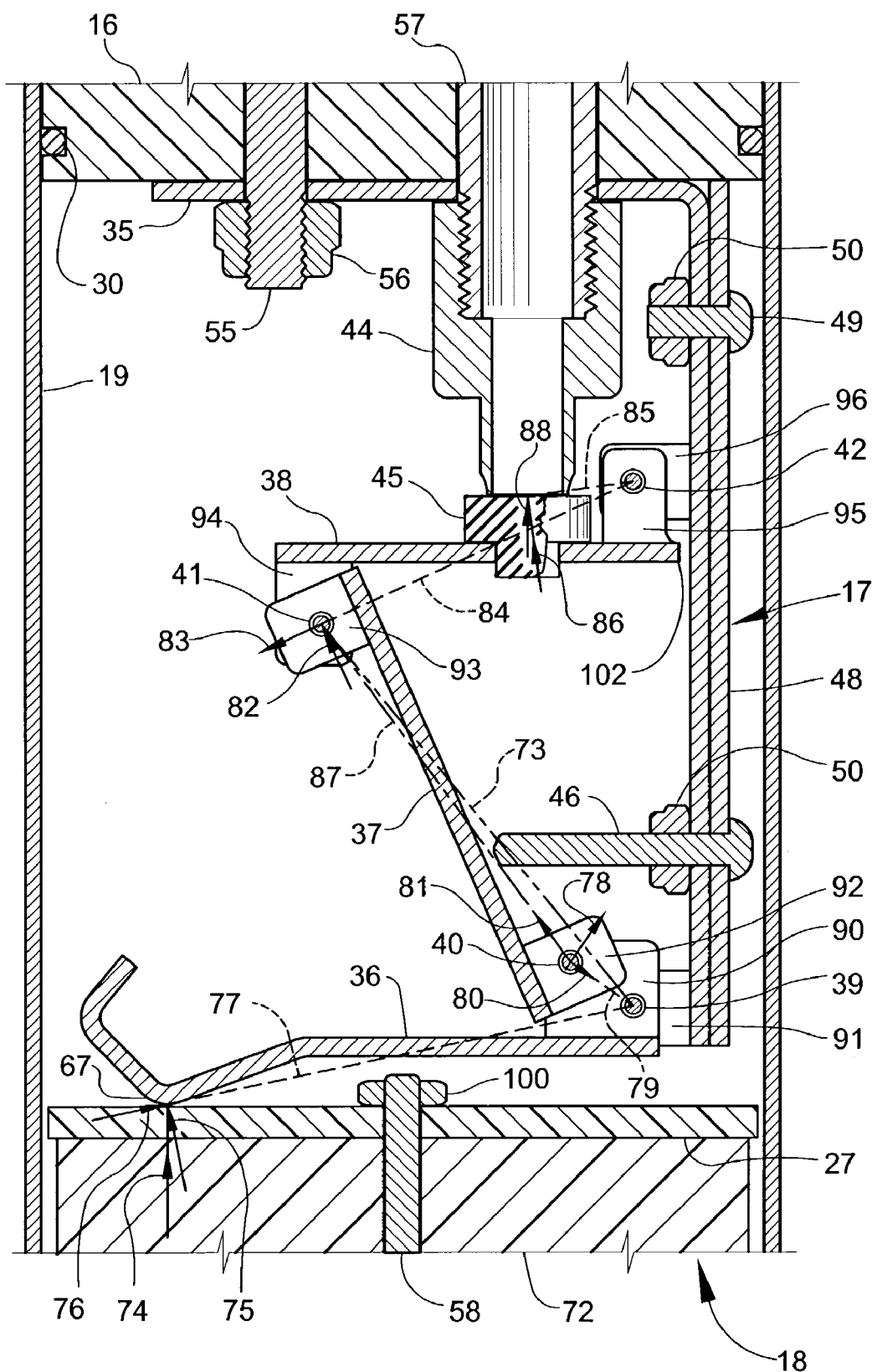
FIG. 8 is an enlarged sectional view of the middle part of the soil permeameter showing the same components as in FIG. 7 but with the valve control assembly in its fully closed position, the force components and the imaginary lines of action being in their changed positions.
Figure 20:
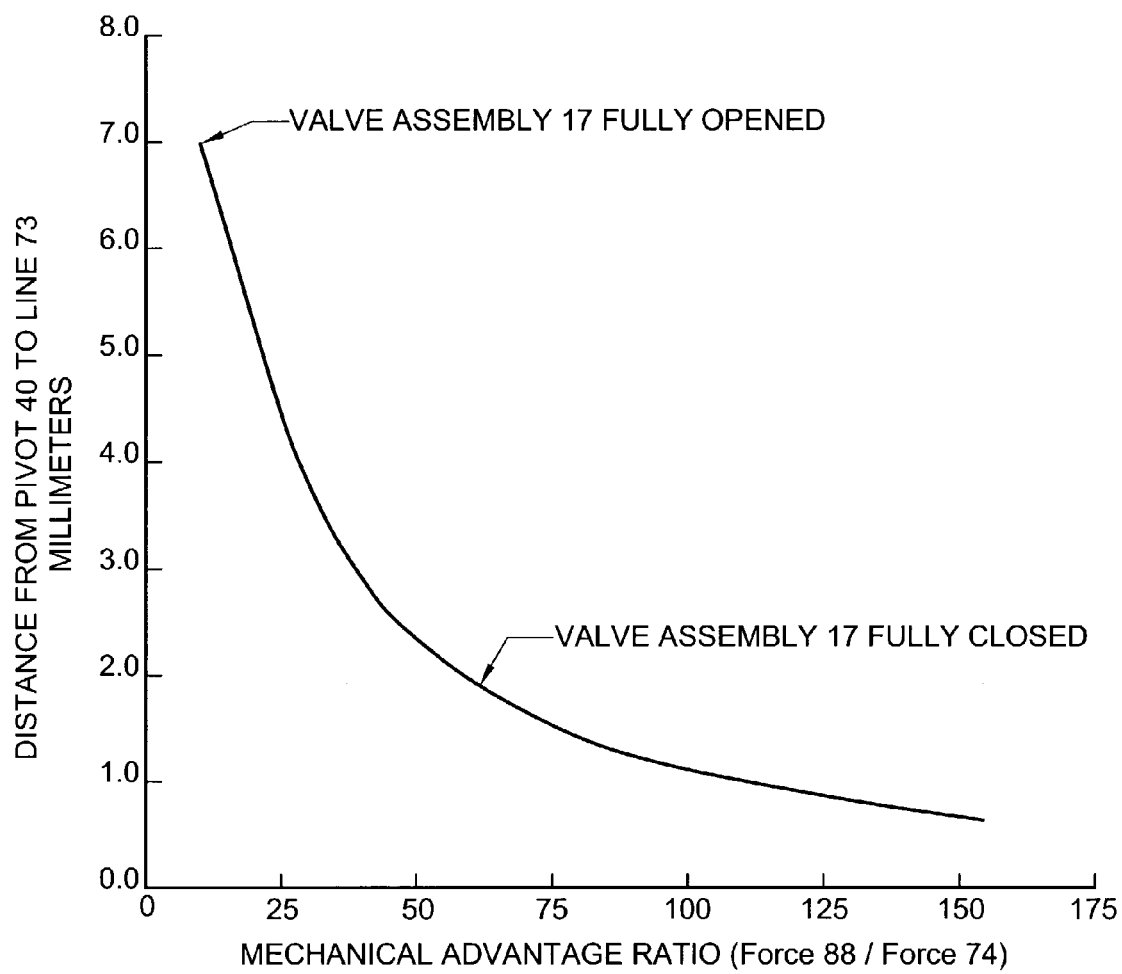
FIG. 20 is a graph of the mechanical advantage ratio, provided by the valve control assembly within the housing.

Force component 88 of force 86 has a line of action through the center of and perpendicular to face 89 of valve seat 45. Force 88, applied at the surface of valve seat 45, provides the force necessary to throttle or stop fluid flow from valve body 44. The mechanical advantage ratio of resultant force 88 to buoyant force 74 ranges from approximately 10:1 at full valve opening (FIG. 7) to approximately 60:1 at full valve closure (FIG. 8). The mechanical advantage (MA) increases as a result of the cumulative mechanical advantages of actuating lever arm 36, link 37, and valve seat retaining lever arm 38. As can be seen in FIG. 20, the mechanical advantage ratio becomes larger at an increasing rate as pivot 40 and line of force 87 approaches, but does not cross, line 73. As the mechanical advantage ratio moves beyond 60:1, the neoprene material in valve seat 45 becomes increasingly compressed.

Within the confines of housing 19, the distance between pivots 39 and 40 is the principal factor controlling amplification of the mechanical advantage ratio beyond 60:1. If the distance of 7.75 mm between pivots 39 and 40, as in the preferred embodiment herein described, is reduced, the torque about pivot 39 is increased in accordance with the ratio of the length of moment arm 77 to the length of moment arm 79, thereby correspondingly increasing resultant force 78. In addition, reduction in distance between pivots 39 and 40 simultaneously increases resultant force component 81 along line of action 87. However, this increased mechanical advantage and increased resultant force comes at a cost because the valve does not open as much as formerly and the maximum fluid flow is less.

The lugs and lever arms are quite rigid while using the preferred 14-gauge stainless steel materials, with a significant safety factor at a depth of even 40 meters. Consequently, the mechanical advantage ratio can be further increased, and the testing depth can thereby be significantly increased beyond 30 meters. The maximum depth of testing for the preferred embodiment described herein is limited to some undetermined depth greater than 40 meters because of limitations imposed by float capacity, fluid pressure, and turbulence created by the incoming water.

Valve control assembly 17 controls the water flow through the permeameter. At the beginning of a typical hydraulic conductivity test, water flows into hose connection 28 of valve control assembly 17 as shown by flow arrow 61 in FIG. 5. Valve control assembly 17 is initially in a fully open position, thereby allowing water flow through valve body 44 and through the opening between valve body 44 and valve seat 45 as shown by flow arrow 62 in FIG. 5.

This water falls on upper float end guide 27 and passes through water flow channels 23 of float assembly 18 and holes 24 of base assembly 60 and continues to flow beneath bottom stopper 20 and into borehole 11, as indicated by flow arrows 63, 64, 65, 66, as seen in FIG. 9.

Figures 5, 6:
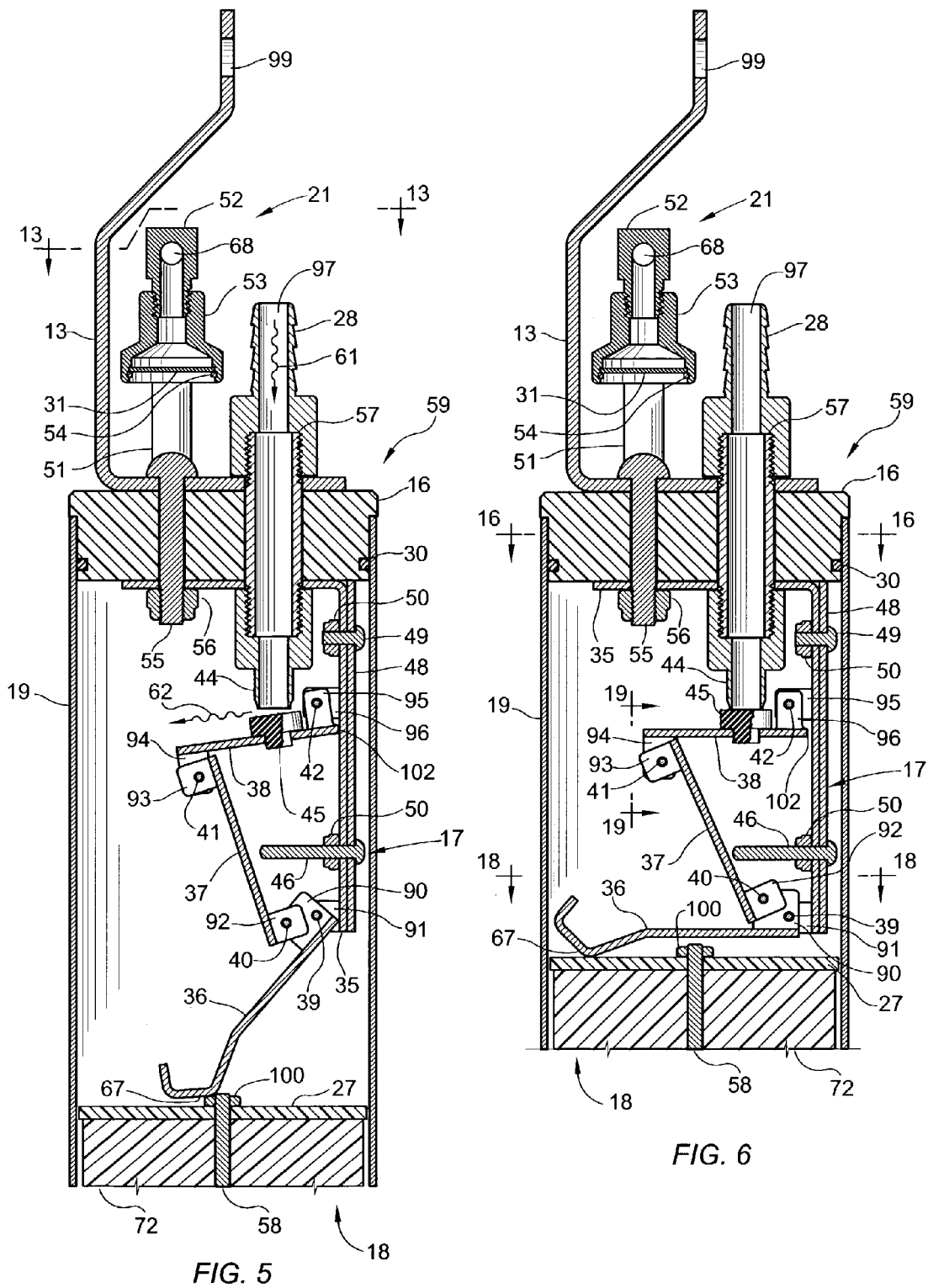
FIG. 5 is a fully sectioned view of the upper part of the constant-head soil permeameter shown in FIGS. 1–3, illustrating the top stopper, its o-ring, the filter vent assembly, the air vent assembly, and the valve control assembly in its fully opened position, a flow arrow emanating from the valve body representing the flow of water into the interior of the cylinder.
FIG. 6 is a sectional view of the upper part of the constant-head soil permeameter showing the same components as in FIG. 5 but with the valve control assembly in its fully closed position, as in FIG. 2.

The water rises at equal corresponding levels in borehole 11 and inside housing 19. As the water level continues to rise, nut 100 of float assembly 18 strikes heel 67 of actuating lever arm 36, which is pivotally connected to valve support bracket 35 at pivot 39, and initiates upward rotation of actuating lever arm 36 around pivot 39. As float assembly 18 continues to rise, forcible contact at heel 67 of actuating lever arm 36 is transferred from nut 50 to float end guide 27, which maintains continuous sliding contact until partial or full valve closure is attained, as seen in FIGS. 1, 2, and 6.

As actuating lever arm 36 rotates upwardly around pivot 39, link 37, which is pivotally connected to pivot 40, revolves around pivot 40 and transfers the buoyant force provided by float assembly 18 to pivot 41 of valve seat retaining lever arm 38. This arm 38 is pivotally connected to valve support bracket 35 at pivot 42. It consequently revolves upwardly and progressively closes the valve opening between valve body 44 and valve seat 45. The mechanical advantage imparted by actuating lever arm 36, link 37, and valve seat retaining lever arm 38 increases with progressive valve closure, as shown in FIG. 20.

Line 73 is an imaginary straight line passing through the centers of pivot 39 and pivot 41, as depicted in FIG. 7. As float assembly 18 rises, heel 67 of actuating lever arm 36 slides from nut 100 onto upper float end guide 27 and continues to slide across guide 27 as actuating lever arm 36 revolves upwardly around pivot 39, thereby moving pivot 40 and link 37 toward line 73. The maximum mechanical advantage is attained just before pivot 40 reaches line 73. Pivot 40, however, is prevented from crossing line 73 by bolt 46, which limits the travel of link 37. The preferred embodiment provides a mechanical advantage ratio of approximately 60:1 at full valve closure.

Float assembly 18 provides the buoyant force required by valve control assembly 17 to throttle water flowing through bore 97 in hose connection 28, pipe 57, and valve body 44. Float assembly 18 moves freely inside housing 19 and is maintained in alignment by both float end guides 27, as shown in FIGS. 5, 6, 11, and 12. The upward travel range of float assembly 18 is limited by contact with valve control assembly 17 and the downward travel range is limited by contact with bolt 29. Prior to application of water during a hydraulic conductivity test, threaded rod 58 of float assembly 18 is at rest on bolt 29, as shown in FIG. 10.

Water added to reservoir 15 during a typical test flows freely around float assembly 18 through flow channels 23 that are disposed longitudinally on float body 72 and float end guides 27, as well as in the annular space between float body 72 and housing 19, as shown in FIG. 12. Bolt 29, which limits downward travel of float assembly 18, prevents float assembly 18 from resting on the upper surface of bottom stopper 20, thereby allowing water applied during the test to flow freely through holes 24, as illustrated in FIGS. 9 and 17 by flow arrows 63, 64, 65, and 66, through bottom stopper 20 and also allowing the water to contact the entire lower surface of float assembly 18 when the water is rising inside housing 19.

Float assembly 18 rises with the rising water and displaces a volume of water equal in weight to the weight of float assembly 18. Float assembly 18 continues to rise in response to the rising water level and strikes heel 67 of actuating lever arm 36 and initiates upward revolution of actuating lever arm 36 around pivot pin 39, as illustrated in FIG. 5. As float assembly 18 continues to rise, contact at heel 67 of actuating lever arm 36 is transferred from nut 100 to upper float end guide 27, which maintains continuous sliding contact until valve throttling control or full valve closure is attained, as seen in FIG. 6. Float assembly 18 becomes partially submerged in proportion to the buoyant force required to throttle water flow from the contact orifice of valve body 44 by valve seat 45, as illustrated in FIG. 32.

As float assembly 18 rises initially, valve seat 45 almost contacts valve body 44 to close bore 97 and stop the flow of water from reservoir 15; then valve seat 45 lowers slightly to establish an equilibrium fluid level in borehole 11 with only a slight fluctuation.

It is desirable to prevent inadvertent backflow entry of water, which may contain suspended soil particles or other debris, into the permeameter. Potential for reverse water flow, as shown by flow arrow 69 in FIG. 10, may occur if the permeameter is placed in a borehole already containing water, if the borehole is advanced further after initial testing and water is not removed, or if the sidewall of the borehole collapses during the test and displaces a sufficient volume of water to cause backflow. Check valve 32 remains closed by pressure differential as long as the water level remains higher in the borehole than in the chamber of housing 19.

Figure 3:
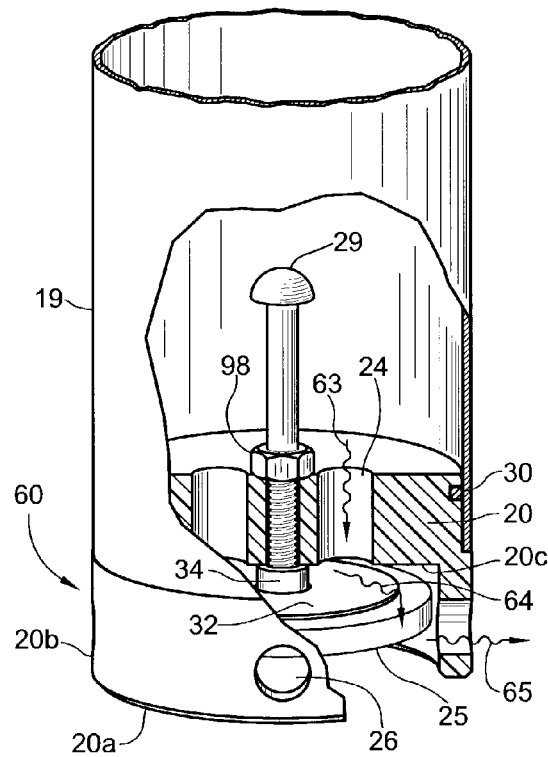
FIG. 3 is an isometric and partial cutout view of the lower part of the constant-head soil permeameter shown in FIGS. 1 and 2, showing the base assembly and the check valve in its open position.
Figure 4:
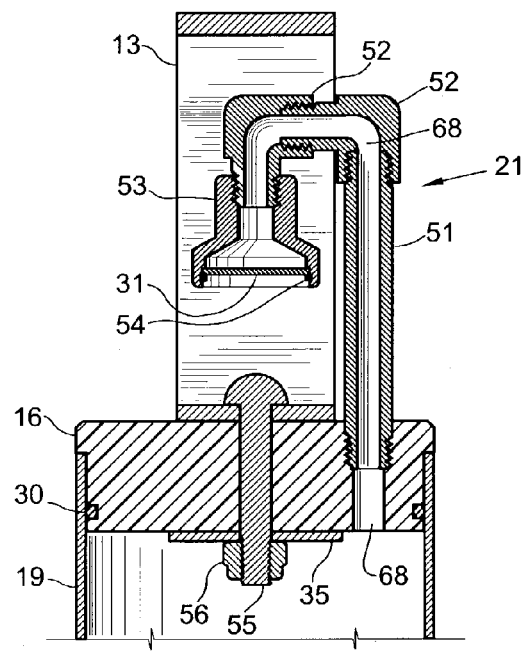
FIG. 4 is a sectional view of the upper part of the same soil permeameter showing the top stopper, the filter vent assembly, and the air vent pathway into the interior of the cylinder, taken along line 4—4 in FIG. 2.

During normal operation, water flows through holes 24 in base assembly 60, as shown by flow arrow 63 in FIGS. 3 and 9, then into the space above check valve 32 and around the annulus between baffle 25 and bottom stopper 20, as shown by flow arrow 64. Water continues to flow through lateral holes 26 of base assembly 60 into the annulus between housing 19 and borehole 11, as shown by flow arrow 65, and into the cavity below baffle 25 as shown by flow arrow 66 in FIG. 9.

Baffle 25 and check valve 32 physically block direct entry of loose soil and other debris into the chamber of housing 19 when the permeameter of the invention is initially placed in the borehole. Bottom stopper 20 also incorporates o-ring 30 to provide a seal between bottom stopper 20 and housing 19, thereby further preventing entry of suspended soil particles and debris. Bottom stopper 20 is countersunk at its bottom 20c to leave a narrow circular rim 20b having a bottom edge 20a, as shown in FIGS. 3 and 9, thereby minimizing the contact area with borehole bottom 11b and providing negligible smearing or blockage of the absorptive soil surface at the bottom of the borehole.

During field operations to determine hydraulic conductivity, an unlined borehole 11 is drilled into the earth to a desired test depth with a suitable drilling or digging device to remove earthen materials and provide an approximately level surface at the bottom of the borehole. The constant-head soil permeameter of the invention is then lowered in a vertical position by cable 12 to rest upon bottom 11b of borehole 11, as shown in FIG. 1. Water is poured into reservoir 15 and flows by gravity through hose 14 and bore 97 in hose connection 28, as shown by flow arrow 61 in FIG. 5, into valve control assembly 17, as shown by flow arrow 62 in FIG. 5. Valve control assembly 17 is initially in a fully open position, thereby allowing water to flow, as shown by flow arrow 62, through the opening between valve body 44 and valve seat 45.

Water then flows onto and around float assembly 18 through channels 23., as seen in FIGS. 2 and 12, into the annular space between float assembly 18 and housing 19 and into the lower part of housing 19. Water next flows through holes 24 in bottom stopper 20, as shown by flow arrow 63 in FIGS. 3 and 9. During normal test procedures, check valve 32 is in its open position which allows water to flow freely through holes 24 in bottom stopper 20 into the space above check valve 32 and around the annulus between baffle 25 and bottom stopper 20, as shown by flow arrows 63 and 64 in FIG. 9. Water then continues to flow through lateral holes 26 in skirt 20b into the annulus between housing 19 and the perimeter of borehole 11, as shown by flow arrow 65 and into the cavity below baffle 25 as shown by flow arrow 66.

Filter vent assembly 21 allows exhausting of air as water rises within housing 19 and maintains atmospheric pressure equally inside and outside of housing 19 within borehole 11 at all times; this pressure equalization between level 22 within housing 19 and height of water H within borehole 11 is essential for maintaining equal water levels inside and outside of housing 19. Filter screen 31 of filter vent assembly 21 also stops entry of loose soil particles into housing 19.

Water rises freely at equal levels within constant-head permeameter 10 and in the annular space between cylindrical housing 19 and the borehole sides until float assembly 18, which is buoyed by the rising water, engages valve control assembly 17. Water flow through valve body 44 is progressively throttled by valve seat 45 of valve control assembly 17 as float assembly 18 continues to rise until water level 22, as seen in FIG. 1, is approximately attained. After a suitable period of time that may vary from several minutes to one-half hour or more depending on soil characteristics, while water from borehole 11 is being transported radially into the surrounding soil matrix 11a, as shown approximately by permeation arrows 47 in FIG. 1, equilibrium water levels H and 22, which are equal, are attained.

The wetting front continues to develop radially from borehole 11 as water levels H and 22 are maintained above the bottom of borehole 11 during the testing period. Water moves radially from borehole 11 through interparticle pores and along voids and fissures that are unique to any particular borehole in response to pressure induced by the constant head of water H, gravitational forces, and capillary forces within the earthen materials. The saturation that occurs within the wetting front during the test period is sometimes referred to as field saturation because some of the voids and pores may contain entrapped air and thereby reduce the potential flow that may occur under fully saturated conditions below the water table. An approximate steady state flow is attained in soil matrix 11a after a period of initial saturation and equilibrium is developed. Water level H is the resultant equilibrium level maintained by permeameter 10 in response to water absorption by soil and a pressure head of water level 70 in reservoir 15, as illustrated in FIG. 1. Once equilibrium of flow is approximately attained, reservoir 15 is filled approximately to initial level 70 in preparation for recording test data.

After initial flow equilibrium is attained, the steady state flow of water absorbed by the soil is determined by recording at discrete time intervals the dropping water levels observed at graduations on reservoir 15. The optimum recording interval varies with the soil type and permeability and is determined by the user. For example, the optimum recording interval for highly permeable sandy soils may be approximately 5 minutes, but for slowly permeable clayey soils may be one-half hour or more. The total time during which observations are recorded may typically vary from on-half hour to 2 hours or more. The flow rate is derived from observations recorded during the selected time period. Level H of water in the borehole may be determined from direct observations or by the use of FIG. 21, which determines level 22 as a function of water flow rate and depth of the permeameter below ground surface 101. The estimated hydraulic conductivity is determined by factoring the steady state flow rate, water depth, and borehole geometry into an appropriate analytical solution.

Solution to Hydraulic Conductivity Values

Figure 21:
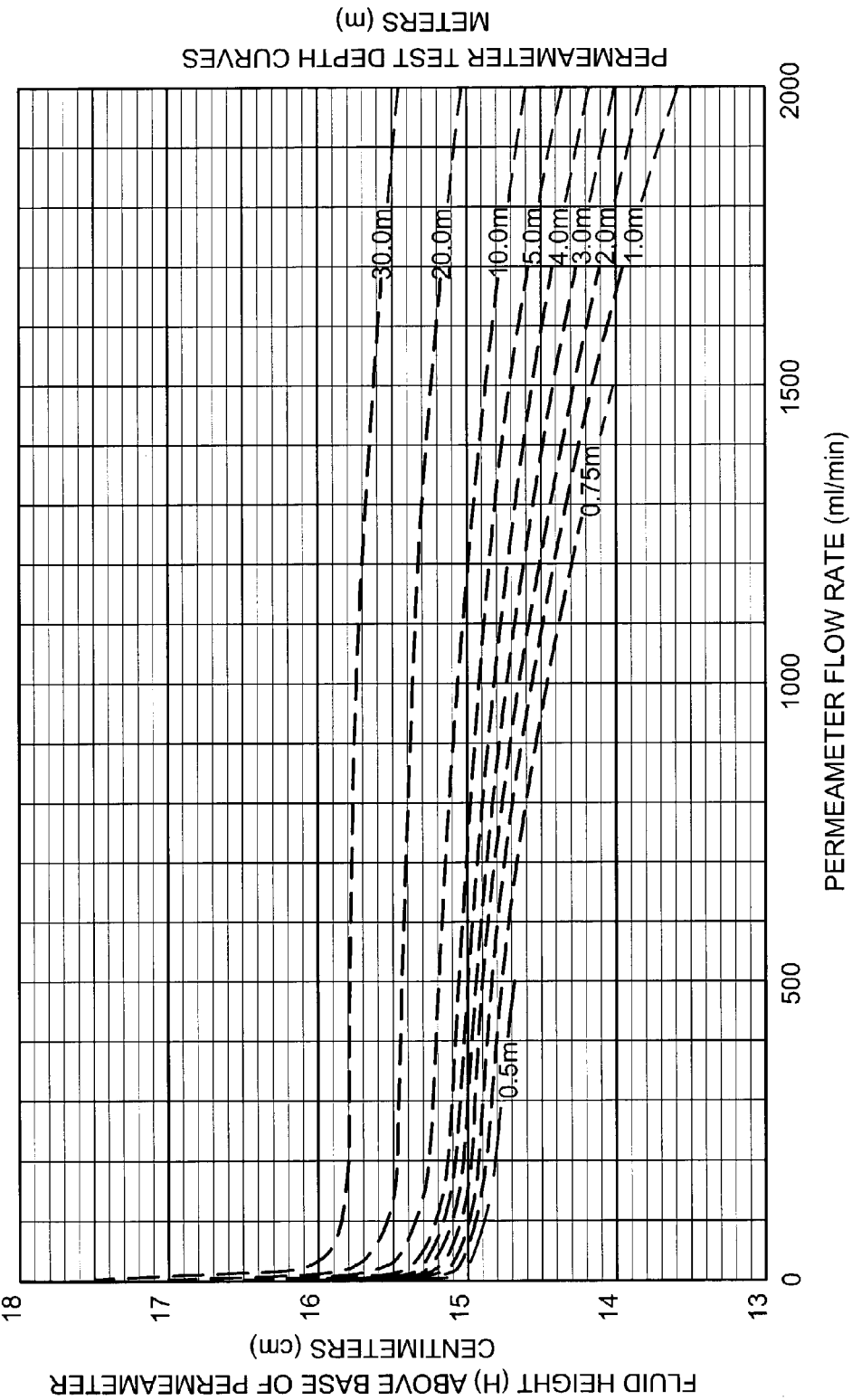
FIG. 21 is a graph containing permeameter test depth-curves for the preferred embodiment of the constant-head soil permeameter of the invention undergoing permeameter flow rates from zero to 2,000 ml/min.

The depth of water, indicated as level H in the borehole, may be determined from direct observations by use of a measuring tape or may be estimated by use of the Flow Rate/Test Depth Chart in FIG. 21. Test depth curves for placement of the permeameter below ground surface 101 range from 0.5 to 30.0 meters, as shown in FIG. 21. The test depth curves of FIG. 21 represent the mean of all observations, 95% of which are within +/−0.5 cm as determined by using an embodiment of the present invention. The test depth curves denote the height of water in the borehole if the permeameter rests on the bottom of the borehole. Alternatively, the permeameter can be suspended at any desired distance above the bottom of the borehole, and the suspended distance beneath rim 20a can be added to the height determined in FIG. 21 to obtain H.

The chart in FIG. 21 can be used to estimate the depth of water within the borehole at any flow rate of the invention ranging from zero to 2000 ml/min. For example, if the permeameter is placed on the bottom of the borehole, the depth of water in the borehole is 10.0 meters, and the flow rate is 500 ml/min., then the estimated depth of the static water level H is approximately 15.2 cm. Where test depths are intermediate to the depth curves of FIG. 21, an appropriate interpolation is made.

The estimated hydraulic conductivity is determined by factoring the steady state flow rate of water into the soil, height of water within the borehole, and borehole geometry into an appropriate analytical solution. One example of an analytical solution has been developed by R. E. Glover (Zangar, 1953). This equation, suggested by Amoozegar and Warrick (1986) for use where the distance between the bottom of the borehole and an impermeable layer is at least twice as large as H, is:

$$K_S = Q[\sinh^{-1}(H/r) - (r^2/H^2 + 1)^{.5} + r/H]/(2\pi 7H^2) \qquad \text{[Equation 1]}$$

Where $K_S$=Saturated hydraulic conductivity,

Q=Steady-state flow rate of water into the soil,

H=Constant height of water in a cylindrical borehole, indicated as level H, and r=Radius of the cylindrical borehole.

Use of this equation is illustrated in the two following examples.

EXAMPLE 1

A cylindrical borehole 11 with diameter of 9.5 cm is augured to a depth of 0.6 meters. It is desired to establish a minimum height H of water equalling 25 cm above the bottom of the borehole, so that the permeameter is suspended 10 cm above the bottom of the borehole. During the test, in which volumetric readings of falling water levels in reservoir 15 are recorded at discrete time intervals spanning a two-hour period, it is determined that the steady-state flow rate of water Q into soil 11a is 5 ml/min. The constant height H of water is, therefore, 25.1 cm (15.1 cm from FIG. 21, plus 10 cm of suspended height). The radius r of borehole 11 is 4.75 cm, and the saturated hydraulic conductivity, $K_s$, from Equation 1 is $3.2 \times 10^{-5}$ cm/sec. This is a low hydraulic conductivity value, typical of silt and clay soils.

EXAMPLE 2

A circular borehole 11 with diameter of 9.5 cm is augured to a depth of 10.0 meters. It is desired to establish a minimum height H of water equalling 25 cm above the bottom of the borehole and to suspend the permeameter at a height of 10 cm above the bottom of the borehole. During a test period of one-half hour, it is determined that the steady-state flow rate of water Q into soil 11a is 900 ml/min. The constant height H of water is, therefore, 25.1 cm (15.1 cm from FIG. 14, plus 10 cm of suspended height). The radius r of the borehole is 4.75 cm and the saturated hydraulic conductivity from Equation 1 is $5.8 \times 10^{-3}$ cm/sec. This is a high hydraulic conductivity value, typical of sandy soils.

In the event that water covers bottom 11b of borehole 11 at the time of inserting the permeameter in borehole 11, check valve 32 of base assembly 60 closes and stops water and suspended soil particles from entering housing 19, as seen in FIG. 10. It is desirable to prevent inadvertent entry of water, which may contain suspended soil particles or other debris, into the permeameter.

This situation may occur if seepage water enters the borehole after it is drilled or if the borehole is advanced to a deeper depth after an initial test has been performed and the remaining water has not been removed during drilling or has not drained completely away into the soil. Water must be removed from the borehole if the initial water levels exceed the equilibrium height of the permeameter. If the water level is a result of seepage or groundwater inflow, the test procedure is invalid because the permeameter is designed to measure hydraulic conductivity as a result of outflow to the soil. Potential reverse water flow may also occur if the sidewall of the borehole collapses during the test and displaces a sufficient volume of water to cause backflow.

FIG. 22 shows a section of the preferred lever-link-lever embodiment which is exactly as shown in FIG. 8 except that the angles, a, b, c, and d are identified therein and are resolved in respective force diagrams, FIGS. 22A, 22B, 22C, and FIG. 22D. Vertically applied force 74, caused by the upward thrust of float assembly 18 upon heel 67, is resolved into force 75 that is perpendicular to imaginary line of action 77, as shown in FIG. 22A. Multiplying force 75 by the length of line 77, functioning as a moment arm, provides a torque force at pivot 39.

Because second pivot 40 passes through lugs 90, this torque force sweeps through pivot 40 and at its center produces force 78 which is resolved in FIG. 22B into force 81 that is exerted along line of action 87 upon third pivot 41. In FIG. 22C, force 81 is resolved into force 82 that is perpendicular to line of action 84 between third pivot 41 and fourth pivot 42.

Multiplying force 82 by the length of line of action 84, functioning as a moment arm, provides a torque force at the center of pivot 42. Then multiplying this force by the ratio of the length of line 84 to line 85, between the center of pivot 42 and the center of valve seat 44, produces force 86 which is perpendicular to line 85. It is resolved in FIG. 22D into a vertically applied resultant force 88 that performs the critical task of stopping the momentum of inwardly flowing water,
closing the valve by contacting body 44 with valve seat 45. Assuming initial force 74 to be 1.00 kg-force, resultant force 88 is 58.71 kg-force.

The equation used is as follows:

Force 88= (Force74)(COS a)(MA77/MA79)(1/COS b)(COS c)(MA84/MA85)(COS d)

When lever arm 36 is moved upwardly beyond the point of closure by one degree past horizontal, the neoprene of valve seat 45 is compressed, causing resultant force 88 to increase to 62.77 kg-force, as given in FIG. 31 in the line identified by **.

In FIG. 23, a second embodiment of the lever-link-lever invention is illustrated in which lugs 90 are slightly lengthened and pivot 40 is moved a small distance toward the center of housing 19 to the position indicated as 40a. The same multiplication of forces by moment arm lengths and resolving of forces in FIGS. 23A, 23B, 23C, and 23D occur to produce the resultant force 88 available for closing valve body 44. Assuming initial force 74 to be 1.00 kg-force, resultant force 88 is 29.20 kg-force.

In FIG. 24, a third embodiment of the lever-link-lever invention is illustrated in which lugs 90 are extended vertically and pivot 40 is moved upwardly and toward the center of housing 19, almost parallel to line 73, to the position indicated as 40b. The same multiplication of forces by moment arm lengths and resolving of forces in FIGS. 24A, 24B, 24C, and 24D occur to produce the resultant force 88 available for closing valve body 44. Assuming initial force 74 to be 1.00 kg-force, resultant force 88 is 70.31 kg-force.

In FIG. 25, a fourth embodiment of the lever-link-lever invention is illustrated in which lugs 90 are considerably lengthened to form lugs 90c and pivot 40 is moved much further toward the center of housing 19 to the position indicated as 40c. The same multiplication of forces by moment arm lengths and resolving of forces in FIGS. 24A, 24B, 24C, and 24D occur to produce resultant force 88 available for closing valve body 44. Assuming initial force 74 to be 1.00 kg-force, resultant force 88 is 12.13 kg-force, as given in FIG. 31.

In FIG. 26, a fifth embodiment of the lever-link-lever invention is illustrated in which lugs 90c and pivot 40c are used, while pivot 41 is moved away from the center of housing 19 to position 41a. The same multiplication of forces by moment arm lengths and resolving of forces in FIGS. 26A, 26B, 26C, and 26D occur to produce resultant force 88 available for closing valve body 44. Assuming initial force 74 to be 1.00 kg-force, resultant force 88 is 17.27 kg-force, as given in FIG. 31.

Figure 27:
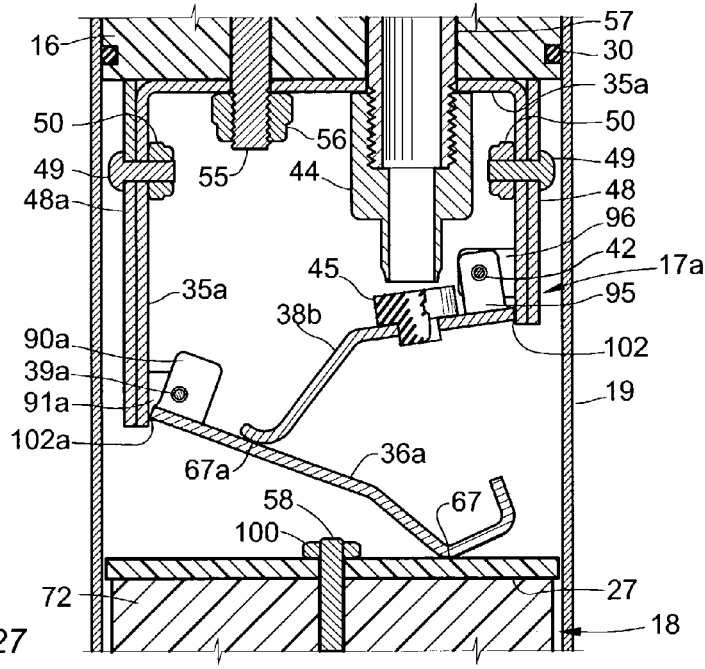
FIG. 27 is a sectional view of a simplified embodiment of the invention that utilizes two lever arms in sliding relationship, the first pivot supporting the actuating lever arm being attached to a valve support bracket and stabilizing bracket on the opposite side of the cylindrical housing to the brackets supporting the second pivot on which revolves the valve seat retaining lever arm having a curved end in sliding contact with the actuating lever arm, with the valve seat being in open position.
Figure 28:
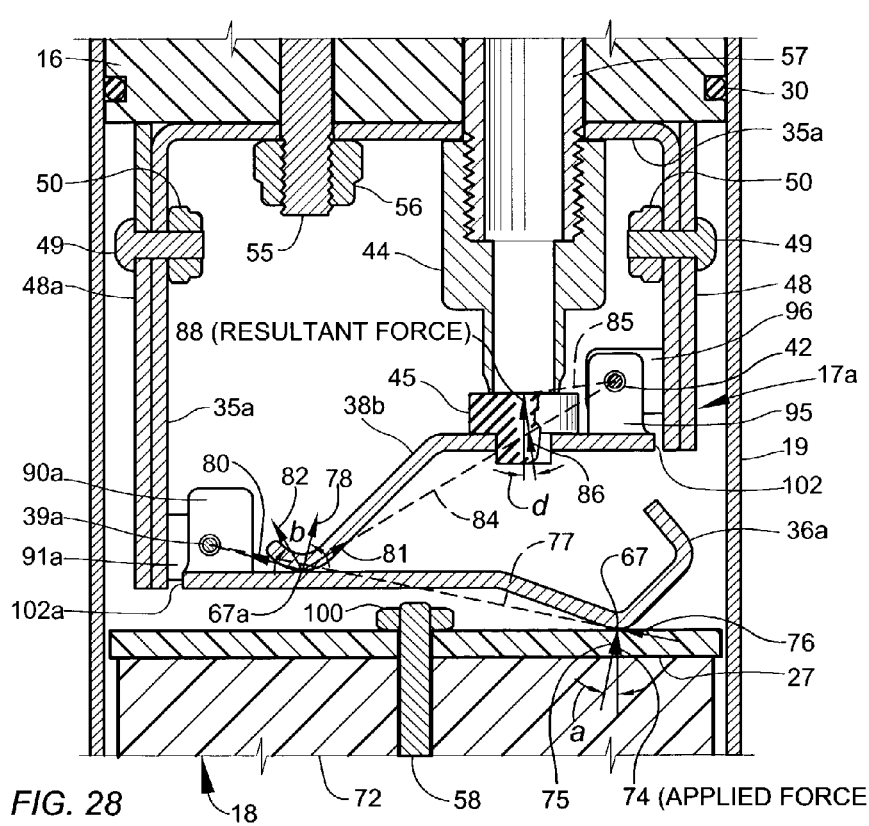
FIG. 28 is a sectional view corresponding to FIG. 27 except that the valve seat is in closed position.
Figure 28C:
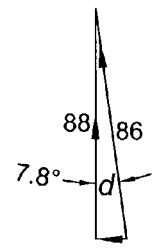
FIG. 28C is a force diagram which resolves the force applied at the center of the valve seat, as the valve seat retaining arm revolves around the second pivot and multiplies the force applied perpendicularly to the second imaginary line of action by the ratio of the length of the second imaginary line of action to the length of a third imaginary line of action, between the second pivot and the center of the valve seat, into a force aligned with this third imaginary line of action and a resultant force which is aligned vertically at the center of the valve body.

FIGS. 27 and 28 show the two-lever or lever-lever embodiment at open and closed valve positions, respectively. In FIG. 27, valve support bracket 35a is extended into a upside-down U shape, and an additional stabilizing bracket 48a is bolted to it on the left side by identical bolt 49 and nut 50. Lug pair 91a is rigidly attached to the lower end of brackets 35a, 48a, and lug pair 90a is attached to lug pair 91a by pivot 39a which is rigidly attached to lever arm 36a having heel 67.

This lever arm 36a, although on the opposite side of cylinder housing 19 as compared to other embodiments, operates in exactly the same way except that the valve formed by valve body 44 and valve seat 45 is fully opened when heel 67 is past nut 100, as shown in FIG. 27. Valve seat retaining lever arm 38b has been modified so that lugs 94 have been removed and the lever arm turned down and then bent slightly upward to provide a rounded sliding contact to act as heel 67a for sliding contact with actuating lever arm 36a. Heel stop 102a, as it contacts bracket 35a, prevents lever arm 36a from dropping too far.

FIG. 28 shows the lever-lever embodiment in its closed position in which lever arm 36a has slid across upper float end guide 27 toward housing 19 sufficiently for valve body 45 to contact valve seat 44 and close the valve.

Figure 28B:
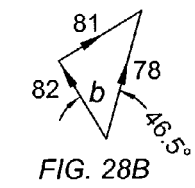
FIG. 28B is a force diagram which resolves the force resulting from the torque produced at the line of sliding contact between the two lever arms into a force exerted perpendicularly to a second imaginary line of action between the this line of sliding contact and the second pivot and a force aligned with this second imaginary line of action.
Figure 28A:
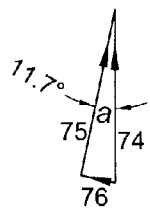
FIG. 28A is a force diagram which resolves the vertically aligned applied force, upon the heel of the lower lever arm, into a force aligned with a first imaginary line of action, between the first pivot and the line of contact of the top of the float body and the heel of the lever arm, and a force aligned perpendicularly thereto.

FIG. 28A resolves applied force 74 into force 75, across an angle of 11.7°, so that force 75 is perpendicular to imaginary liner of action 77 between line of contact 67 and line of contact 67a where, as shown in FIG. 28B, applied force 78 is resolved across an angle of 46.5° into force 82 which is perpendicular to imaginary line of action 84 between line of contact 67a and pivot 42. This results in applied force 86 which is perpendicular to imaginary line of action 85 between pivot 42 and the center of seat 45. Resolving force 86 across angle d of 7.8° provides resultant force 88. Assuming initial force 74 to be 1.00 kg-force, resultant force 88 is 11.49 kg-force, as given in FIG. 31.

In FIG. 29, a one-lever embodiment of the invention is illustrated in which lugs 95, 96 and pivot 42 are used to support valve seat retaining arm 38c which has been modified to have a heel like heel 67 in lever arm 36. Arm 38c functions as does arm 36 in other embodiments by initially resting on nut 100 and then sliding across upper float end guide 27 as float 18 rises. FIG. 29 shows the valve 44, 45 in fully closed position. The same multiplication of forces by moment arm lengths and resolving of forces in FIGS. 29A and 29B occur to produce resultant force 88 available for closing valve body 44 with valve seat 45. Assuming initial force 74 to be 1.00 kg-force, resultant force 88 is 4.33 kg-force, as given in FIG. 31.

FIG. 30 is an embodiment utilizing all of the components of the constant-head permeameter, particularly as shown in FIG. 29, except that lever arm 38d has been drastically modified. Lever arm 38d comprises a dipper-shaped arm which is rigidly attached to lug pairs 95 that are in movable engagement with lug pairs 96 through both of which pivot 42 passes. The bottom of lever arm 38d contacts the top surface of float end guide 27, and its cup pivotably supports valve seat 45, so that valve 44, 45 controlling the water inlet means is fully closed when float 18 has sufficiently risen, but without application of any closing leverage other than force 74, thus simulating the prior art, because applied force 74 and resultant force 88 are equal and in vertical alignment. As shown in FIG. 31, if initial force 74 is 1.00 kg-force, resultant force 88 is also 1.00 kg-force.

FIG. 31 contains two tables of calculated data to show the relationship of forces. The upper table relates to the lever-link-lever embodiments in which the second pivot is in four selected positions and the third pivot is in one different position in combination with one of the alternate positions for the second pivot. The first line for FIG. 22 represents the preferred embodiment.

The lower table in FIG. 31 contains calculated data for the two-lever, the single lever, and the prior art embodiments. The wide range of magnification that is obtainable by using the principles of this invention is amply demonstrated in these two tables.

FIG. 32 shows two drawings of the float body used in all embodiments of the invention, as well as in the prior art embodiment shown in FIG. 30, to illustrate the float submersion required to stopper the valve at various pressure heads of water for the lever-link-lever and the two-lever embodiments at the left float and for the single lever and prior art embodiments at the right float as the float bodies are submerged in surrounding water within the cylindrical housing, with depths of float submergence in centimeters being indicated by the central scale and the pressure heads of water in meters being marked on each side of each float.

Figure 33:
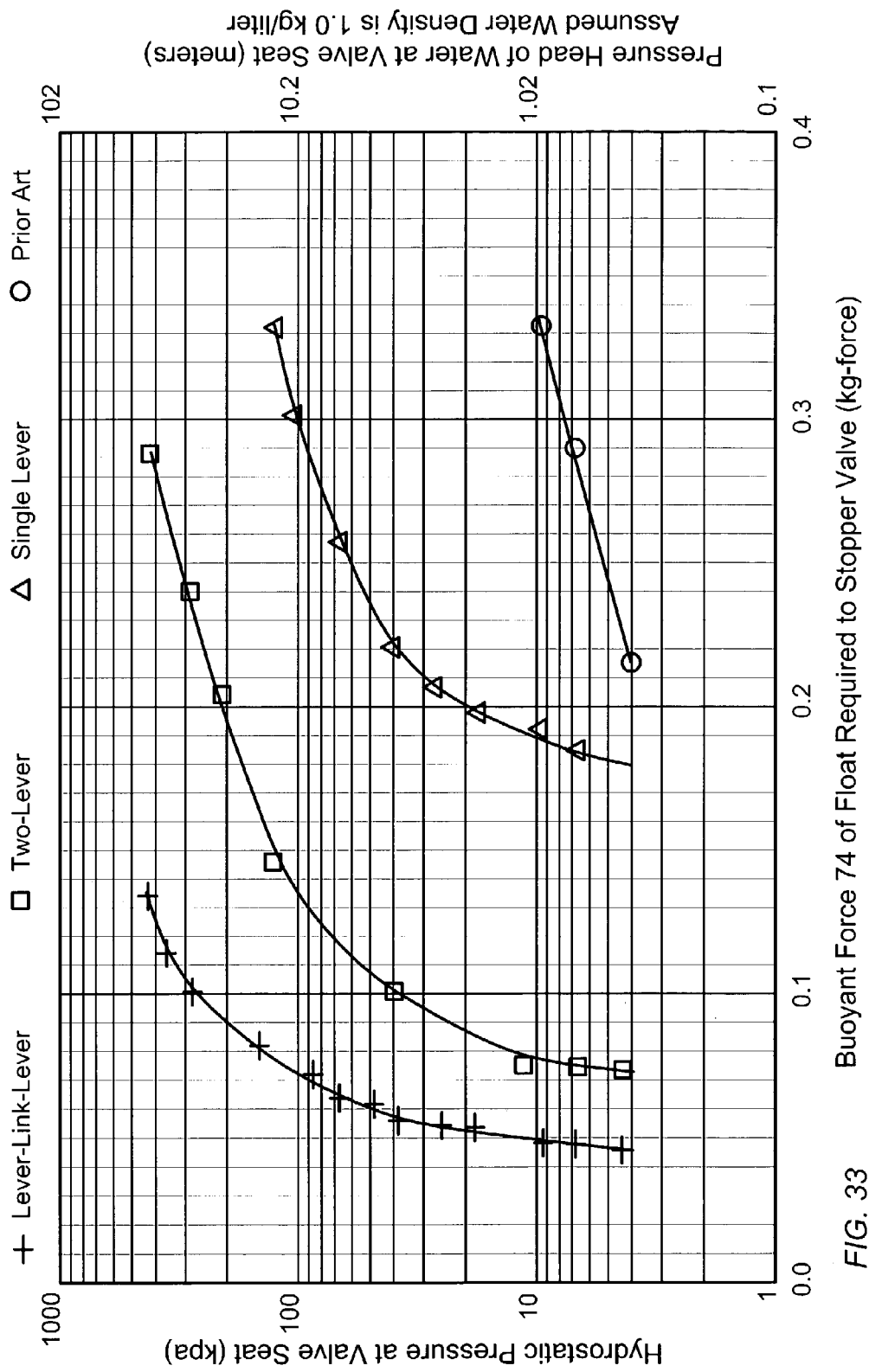
FIG. 33 is a semi-logarithmic graph for the hydraulic pressure at the valve seat (pressure head, as in FIG. 1) versus the buoyant force required to stopper the valve, the four curves representing the lever-link-lever embodiment, the two-lever embodiment, the single-lever embodiment, and the prior art embodiment.

FIG. 33 is a semi-logarithmic chart on which curves for four types of valve control assemblies are displayed. These are: 1) lever-link-lever, 2) two-lever, 3) single lever, and 3) prior art. Each of these four embodiments was constructed as hereinbefore descibed and tested. The prior art has not used any lever to provide a mechanical advantage for stoppering the valve seat, and this prior art embodiment illustrates that fact.

On the left ordinate is the hydrostatic pressure at the valve seat in kilopascals. On the right ordinate is the comparable pressure head of water at the valve seat in meters. On the abscissa is the buoyant force (kilogram-force or kg-force) required to stopper fully the flow from the valve seat at various depths ranging from 0.75 meter to approximately 41 meters.

Figure 34:
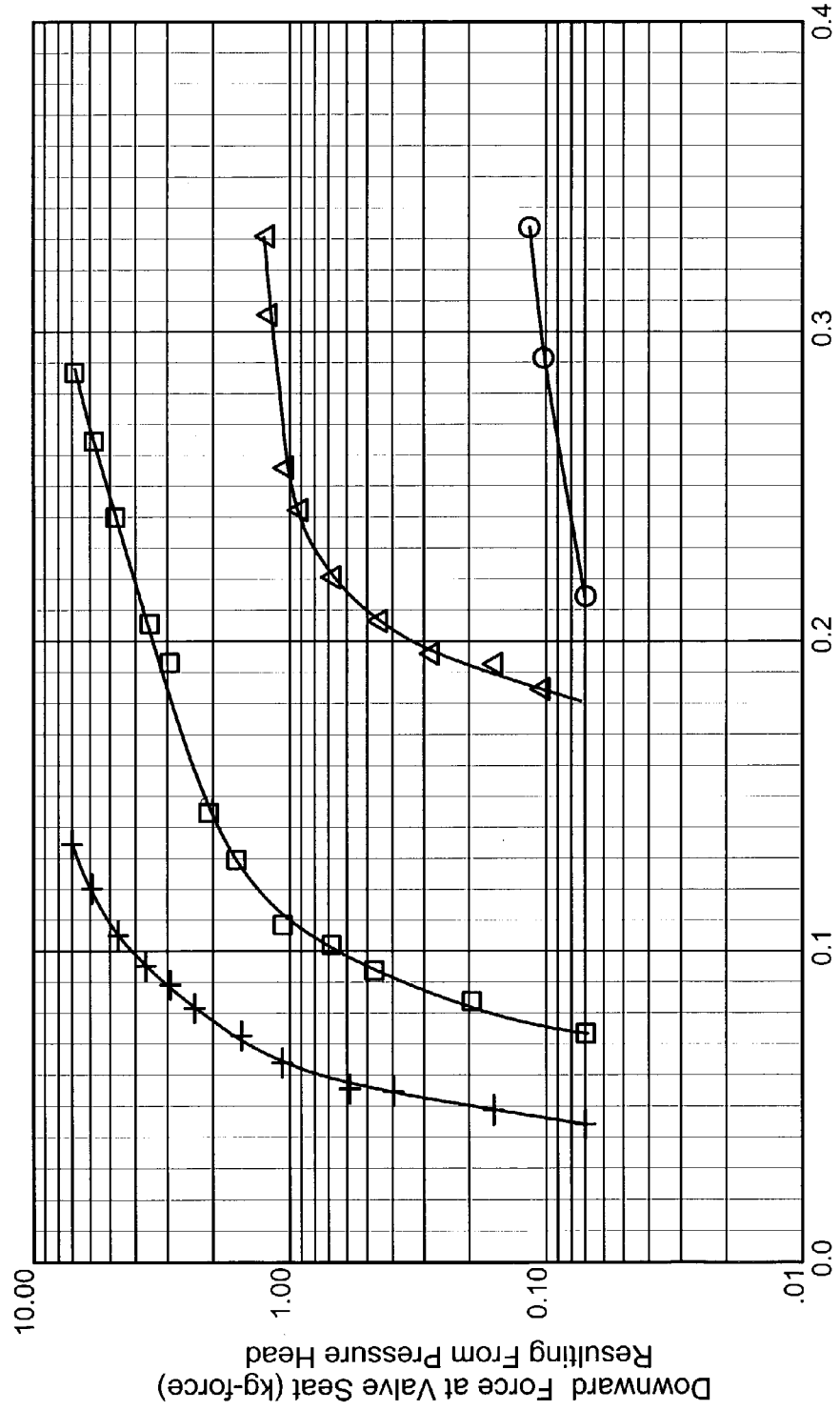
FIG. 34 is a semi-logarithmic graph for the downward force at the valve seat, calculated as the hydrostatic pressure only and not including the momentum and other fluid-flow forces, versus the buoyant force required to stopper the valve.

FIG. 34 is a semi-logarithmic graph which also displays curves for the four valve control assemblies. These curves, which are based on the same empirical test results as shown in FIG. 33, show the downward resultant forces of the hydrostatic pressure at valve 44, 45 that must be overcome to fully stopper flow from the valve for each embodiment. The valve body bore diameter is 0.715 cm, and the valve seat composition is the same for all embodiments. The downward resultant force at the valve seat is shown on the ordinate in kg-force, and the corresponding buoyant force to stopper the downward flow is also shown on the abscissa in kg-force.

The values for each embodiment and for the prior art were determined empirically, using water pressure available in Fairfax county, Va., in simulated tests. The same housing 19, float assembly 18, float body 72, and orientation were used for each test. Float assembly 18 comprised a buoyant core 72, rigid end caps 27, bolt 58 through the center of float body 72, and channels 23 for free water flow. The float was approximately 11 cm in length, including the end caps (each 0.318 cm or ⅛ inch in thickness). The diameter of buoyant core 72 was approximately 6.9 cm. The cross-sectional area of core 72 was 36.33 sq. cm.

A column of water within a 10.16-cm (4-inch) diameter cylinder was used to establish the pressure head for a height ranging from 0.75 m to 1.25 m. A water line source (tap water), with three pressure regulators of different ranges and a bank of three pressure gauges of different ranges, was used to establish a pressure head equivalent to a height of up to approximately 41 meters. The gauges were positioned in elevation to provide correct pressure readings for depths corresponding to the bottom of permeameter housing 19. However, for these comparative tests shown in the graph, an adjustment of 0.31 meter was used to determine the pressure at as close to the face of valve body 44 as possible.

Float assembly 18 became submersed to a depth of 1.5 cm under its own weight. The net buoyant force required to stopper the valves for each embodiment and depth was provided by the buoyant force of the float, as water rose and increased the buoyant force until pressure at the seat of valve body 44 became sufficient to stopper the inward flow completely. The submersed depth was measured and then converted to volume. Archimedes Principle was then used to determine the net resultant buoyant force. The net buoyant force is shown on the abscissa of the graph.

As seen in the graph of FIG. 33, the lever-link-lever embodiment, which has a mechanical advantage of approximately 60:1 at full closure, stoppered flow at a hydrostatic pressure of approximately 410 KPa and required a buoyant force of 0.105 Kg-force. The lever-lever embodiment, which has a mechanical advantage of approximately 11:1 at full closure, stoppered flow at a hydrostatic pressure of approximately 410 KPa and a buoyant force of 0.29 Kg-force. The maximum pressure attainable in the local water service was just over 410 KPa so that higher hydrostatic pressures might have been achieved if higher water pressures had been available.

The one-lever embodiment, which has a mechanical advantage of approximately 4.3:1 at full closure, stoppered flow at a hydrostatic pressure of approximately 121 KPa and a buoyant force of 0.33 Kg-force. The float became almost totally submerged at this point.

The no-lever embodiment (prior art), which has no mechanical advantage, stoppered flow at a hydrostatic pressure of approximately 9 KPa and a buoyant force of 0.33 Kg-force. The float became almost totally submerged at this point. The maximum effective depth was approximately one meter. It was also noticeable that it took several minutes for the water to stop flowing and for the valve 44, 45 to stabilize.

The water was introduced into each of the cylinders 19 at a moderate flow rate. During previous tests, it was noted that the flow of the lever-link-lever permeameter pulsed somewhat at high flow rates, such as higher than 2,000 ml/minute, and at high pressures corresponding to depths greater than approximately 30 meters for the lever-link-lever embodiment. This phenomenon was probably due to the dynamics caused by the high pressure and flow rate.

The lever-link-lever embodiment is the most efficient of the embodiments, because its mechanical advantage dynamically changes in a manner that allows full valve openings over a range of pressures, yet it provides the maximum mechanical advantage at full closure where it is most necessary.

Because it will be readily apparent to those skilled in the constant-head soil permeameter art that innumerable variations, modifications, applications, and extensions of the principles hereinbefore set forth can be made without departing from the spirit and the scope of the invention, what is hereby defined as such scope and is desired to be protected should be measured, and the invention should be limited, only by the following claims.

What is claimed is:

1. A constant-head soil permeameter, comprising a cylindrical housing having a top stopper and a bottom stopper, a float assembly disposed within said housing, means for enabling air to flow into and out of said housing, means for introducing a liquid through said top stopper to a valve comprising a valve seat and a valve body within said housing, and a valve control assembly which provides a mechanical advantage ratio for closing said valve and thereby shutting off said introducing of liquid into said housing.

2. The constant-head soil permeameter of claim 1, wherein said valve control assembly comprises two lever arms, an intervening link, four pivots, and seven pairs of lugs.

3. The constant-head soil permeameter of claim 2, wherein said mechanical advantage ratio is selectively variable according to selected lengths of said lever arms and of said link and according to selected placements of said pivots.

4. The constant-head soil permeameter of claim 3, wherein said mechanical advantage ratio ranges from approximately 10:1 at full valve opening up to a ratio within the range of 12:1 to 70:1 at full valve closure, while utilizing a hydrostatic pressure of approximately 410 KPa and a required buoyant force of 0.105 Kg-force.

5. The constant-head soil permeameter of claim 4, wherein:
  A) said float assembly comprises a buoyant float body having upper and lower lid surfaces; and
  B) said permeameter further comprises a valve support bracket which is rigidly attached to said top stopper and comprises a portion within said housing which is longitudinally disposed and has a lower end forming a stop for upward motion of said upper lid surface.

6. The constant-head soil permeameter of claim 5, wherein said buoyant float body comprises means for allowing said liquid to flow to and through said lower lid surface.

7. The constant-head soil permeameter of claim 6, wherein said bottom stopper comprises means for preventing backflow of said liquid from said borehole into said cylinder.

8. The constant-head soil permeameter of claim 5, wherein a first said lug pair of said seven pairs of lugs is rigidly attached to said bracket portion at said lower end thereof and a second said lug pair is rigidly attached to said bracket portion in close proximity to said valve.

9. The constant-head soil permeameter of claim 8, wherein:
  A) one said lever is an actuating lever arm having a heel near one end and a third said lug pair at its other end, said third lug pair being in side-by-side movable engagement with said first lug pair on a first pivot passing through both said lug pairs;
  B) said intervening link is disposed semi-vertically when said heel is not in contact with said upper lid surface and has a fourth said lug pair at its lower end and a fifth said lug pair at its upper end, said lug pairs facing in opposite directions and said fourth lug pair being in side-by-side movable engagement with said third lug pair on a second said pivot passing through both said third and fourth lug pairs; and
  C) the second said lever is a valve seat retaining lever arm which is generally horizontally disposed and has:
    1) a sixth lug pair at its inner end which is in side-by-side movable engagement with said fifth lug pair on a third said pivot passing through both said fifth and sixth lug pairs, and
    2) a seventh lug pair at its outer end, said sixth and seventh lug pairs facing in opposite directions, and said seventh lug being in side-by-side movable engagement with said second lug pair on a fourth said pivot passing through both said seventh and second lug pairs.

10. The constant-head soil permeameter of claim 9, wherein the effective testing depth range of said permeameter is from 15 centimeters to about 30 meters.

11. The constant-head soil permeameter of claim 9, wherein the permeability testing range of the permeameter is from $10^{-6}$ centimeters/second to $10^{-2}$ centimeters/second.

12. The constant-head soil permeameter of claim 9, wherein the range of liquid flow volume through said permeameter is from zero to at least 2000 milliliters/minute at depths greater than one meter.

13. A constant-head soil permeameter, for measuring hydraulic conductivities of soils inside a borehole at a variety of depths ranging from shallow to deep, comprising a cylindrical housing having a narrow interior diameter and, operably disposed within said housing, at least one lever arm and at least one pivot as a magnifying means for increasing an applied force for shutting off liquid flow into said housing.

14. The constant-head soil permeameter of claim 13, wherein said permeameter additionally comprises a float assembly, disposed within said housing, which comprises a buoyant float body which is axially movable within said housing, said applied force being the upward thrust created by said float assembly which rises while a liquid level rises within said housing.

15. The constant-head soil permeameter of claim 14, wherein:
   A) said narrow interior diameter is approximately seven centimeters; and
   B) said housing additionally comprises an axis, a top stopper, and a bottom stopper, means for enabling air to flow into and out of said housing through said top stopper, means for introducing a liquid through said top stopper to a valve comprising a valve seat and a valve body within said housing, and a valve control assembly, as said magnifying means, which provides a selectively variable mechanical advantage ratio of resultant force divided by said applied force, for closing said valve and thereby shutting off said introducing of liquid into said housing when liquid levels within said housing and within said bore hole, outside of said housing, are in equilibrium.

16. The constant-head soil permeameter of claim 15, wherein said valve control assembly comprises:
   A) an actuating lever arm having a pressure end and a pivot end, said pressure end having a heel which is in contact with said buoyant float body to receive said applied force, and said pivot end having a rigidly attached second pair of lugs in movable relationship with a first pair of lugs on a first pivot passing through both said first and second pairs of lugs;
   B) a third pair of lugs in movable relationship with said second pair of lugs on a second pivot passing through both said second and third pairs of lugs;
   C) a link, rigidly attached to said third pair of lugs at its lower end and having a fourth pair of lugs rigidly attached at its upper end in movable relationship with a fifth pair of lugs on a third pivot passing through both said pairs of lugs; and
   D) a valve body retaining lever arm having said fifth pair of lugs rigidly attached to its axis end and a sixth pair of lugs rigidly attached to its housing end in movable relationship with a seventh pair of lugs on a fourth pivot passing though both said pairs of lugs, said first and said seventh pairs of lugs being attached to a valve support bracket which is rigidly attached to said top stopper and longitudinally disposed adjacent said housing;
all said lugs being spaced apart and said link and both said lever arms having a width corresponding to said spaced-apart lugs, whereby rigidity is imparted throughout said valve control assembly, said second pivot being in a preferred position which is approximately 0.85 cm from said first pivot, whereby said mechanical advantage ratio is approximately 59.

17. The constant-head soil permeameter of claim 16, wherein said second pivot is placed approximately 0.24 cm toward said axis from said preferred position of said second pivot, whereby said mechanical advantage ratio is approximately 29.

18. The constant-head soil permeameter of claim 16, wherein said third pair of lugs is lengthened toward said top stopper and said second pivot is placed approximately 0.89 cm and about 45° upwardly and toward said axis from said preferred position of said second pivot, whereby said mechanical advantage ratio is approximately 70.

19. The constant-head soil permeameter of claim 16, wherein said heel of said actuating lever arm has moved toward said top stopper by one degree under increasing pressure from said float body after said valve has been closed, thereby compressing neoprene material in said valve body, whereby said mechanical advantage ratio is approximately 63.

20. The constant-head soil permeameter of claim 16, wherein said third pair of lugs is lengthened toward said axis and said second pivot is placed approximately 0.81 cm toward said axis from said preferred position of said second pivot, whereby said mechanical advantage ratio is approximately 12.

21. The constant-head soil permeameter of claim 20, wherein said second pivot is unchanged, said third pivot is placed approximately 0.81 cm closer to said axis, and said valve seat retaining arm is lengthened by 0.81 cm, whereby said mechanical advantage ratio is approximately 17.

22. In a constant-head soil permeameter, comprising a narrow cylindrical housing having a top stopper and a bottom stopper, a buoyant float body having upper and lower lid surfaces which is axially movable within said housing, and means for introducing a liquid through said top stopper to a valve comprising a valve seat and a valve body, the improvement comprising:
   a support bracket which is rigidly attached to said top stopper and extends longitudinally alongside said housing, a first pair of lugs rigidly attached to said bracket, a lever arm, having a pressure end and a pivot end which has a rigidly attached second pair of lugs in movable relationship with said first pair of lugs on a first pivot passing through both said first and second pairs of lugs, said valve body being attached to said lever arm in facing relationship to said valve seat and said pressure end being in slidable contact with said upper lid surface of said float body, whereby upward movement of said float body creates an applied force which is magnified by said lever arm.

23. The improvement of claim 22, wherein said force is magnified approximately 4.33 times at said valve seat when said float body is substantially submerged.

24. The improvement of claim 22, wherein said float body comprises means for allowing said liquid to flow to and through said lower lid surface.

25. The improvement of claim 24, wherein said bottom stopper comprises means for allowing said liquid to flow through said stopper and outwardly into a borehole surrounding said housing.

26. The improvement of claim 25, wherein said bottom stopper comprises means for preventing backflow of said liquid from said borehole into said cylinder housing.

27. A constant-head soil permeameter, comprising a cylindrical housing having a top stopper and a bottom stopper, a buoyant float body having upper and lower surfaces which is axially movable within said cylinder, means for enabling air to flow into and out of said cylinder, means for introducing a liquid through said top stopper to a valve comprising a valve seat and a valve body, a U-shaped bracket which is rigidly attached to said top stopper and extends longitudinally alongside said housing on opposite sides thereof, a first pair of lugs which is rigidly attached to said bracket on one said side, a second pair of lugs which is rigidly attached to said bracket on the other said side, a valve seat retaining lever arm having a pivot end and a slide end, said pivot end having a third pair of lugs in movable engagement with said first pair of lugs on a first pivot passing through both said first and second pairs of lugs, an actuating lever arm having a pivot end and a sliding contact end, said pivot end having a fourth pair of lugs which is rigidly attached thereto and is in movable engagement with said second pair of lugs on a second pivot passing through both said second and fourth pairs of lugs, whereby said slide end slidably engages said actuating lever arm and said sliding contact end slidably engages said top surface of said float body to provide two stages of leverage for magnifying said initial force created by upward movement of said float body into a resultant force capable of closing said valve.

28. The two-lever constant-head soil permeameter of claim 27, wherein said resultant force is 11.49 times said initial force when said float body is substantially submerged.

* * * * *